United States Patent
Lyons et al.

(10) Patent No.: US 11,918,823 B2
(45) Date of Patent: Mar. 5, 2024

(54) SINGLET OXYGEN GENERATING DEVICE FOR SELECTIVE DESTRUCTION OF PATHOGENS

(71) Applicants: Research Foundation of the City University of New York, New York, NY (US); SingletO2 Therapeutics LLC, New Providence, NJ (US)

(72) Inventors: Alan M. Lyons, New Providence, NJ (US); Alexander Greer, New York, NY (US); QianFeng Xu, Staten Island, NY (US)

(73) Assignees: Research Foundation of the City University of New York, New York, NY (US); SingletO2 Therapeutics LLC, New Providence, NJ (US)

( * ) Notice: Subject to any disclaimer, the term of this patent is extended or adjusted under 35 U.S.C. 154(b) by 708 days.

(21) Appl. No.: 17/099,273

(22) Filed: Nov. 16, 2020

(65) Prior Publication Data

US 2021/0138258 A1    May 13, 2021

Related U.S. Application Data

(63) Continuation-in-part of application No. 15/729,005, filed on Oct. 10, 2017, now Pat. No. 10,835,629.

(Continued)

(51) Int. Cl.
*A61N 5/06* (2006.01)
*A61K 41/00* (2020.01)
(Continued)

(52) U.S. Cl.
CPC ........ *A61N 5/0603* (2013.01); *A61K 41/0057* (2013.01); *A61L 2/18* (2013.01);
(Continued)

(58) Field of Classification Search
CPC .. A61N 5/0603; A61N 5/062; A61K 41/0057; A61L 2/18; A61L 2/26; A61C 1/0046; A61C 5/40
See application file for complete search history.

(56) References Cited

U.S. PATENT DOCUMENTS 5,611,793 A * 3/1997 Wilson .................... A61P 43/00
606/2
5,658,148 A * 8/1997 Neuberger ............. A61N 5/062
433/29

(Continued)

FOREIGN PATENT DOCUMENTS

WO    WO0110327    2/2001

OTHER PUBLICATIONS

Bartusik, D. et al.; Bacterial Inactivation by a Singlet Oxygen Bubbler: Identifying Factors Controlling the Toxicity of 1O2 Bubbles; Environmental Science & Technology; Oct. 18, 2012; pp. 12098-12104; vol. 46; ACS Publications.

(Continued)

*Primary Examiner* — Nicholas D Lucchesi
(74) *Attorney, Agent, or Firm* — Peter J. Mikesell; Schmeiser, Olsen & Watts, LLP

(57) ABSTRACT

A device for generating singlet oxygen is provided. The device has a sensitizer that converts triplet oxygen to single oxygen upon exposure to light. The device is configured to keep the sensitizer from contacting external fluids.

16 Claims, 26 Drawing Sheets

Related U.S. Application Data

(60) Provisional application No. 62/405,583, filed on Oct. 7, 2016.

(51) Int. Cl.

| | | |
|---|---|---|
| *A61L 2/18* | (2006.01) | |
| *A61L 2/26* | (2006.01) | |
| *C02F 1/50* | (2023.01) | |
| *C02F 1/72* | (2023.01) | |
| *A01K 61/13* | (2017.01) | |
| *A01K 63/04* | (2006.01) | |
| *A01K 63/06* | (2006.01) | |
| *C02F 103/20* | (2006.01) | |

(52) U.S. Cl.
CPC ............... *A61L 2/26* (2013.01); *A61N 5/062* (2013.01); *C02F 1/50* (2013.01); *C02F 1/727* (2013.01); *A01K 61/13* (2017.01); *A01K 63/042* (2013.01); *A01K 63/06* (2013.01); *A61L 2202/11* (2013.01); *A61N 2005/0606* (2013.01); *A61N 2005/063* (2013.01); *A61N 2005/0644* (2013.01); *A61N 2005/0645* (2013.01); *C02F 2103/20* (2013.01); *C02F 2303/04* (2013.01)

(56) References Cited

U.S. PATENT DOCUMENTS

| | | | | |
|---|---|---|---|---|
| 7,306,459 | B1* | 12/2007 | Williams | A61C 5/50 433/29 |
| 8,450,359 | B2 | 5/2013 | McCoy et al. | |
| 9,987,200 | B2* | 6/2018 | Kishen | A61N 5/0624 |
| 11,350,993 | B2* | 6/2022 | DiVito | A61N 5/0624 |
| 2003/0059379 | A1* | 3/2003 | Andersen | A61N 5/062 514/297 |
| 2004/0224288 | A1* | 11/2004 | Bornstein | A61C 5/50 433/29 |
| 2007/0031819 | A1* | 2/2007 | Koschwanez | G01N 33/585 382/128 |
| 2007/0225559 | A1* | 9/2007 | Clerc | A61B 1/018 600/113 |
| 2008/0070195 | A1* | 3/2008 | DiVito | A61C 5/50 433/224 |
| 2008/0255498 | A1* | 10/2008 | Houle | A61C 17/0208 604/20 |
| 2009/0012587 | A1 | 1/2009 | Wang et al. | |
| 2009/0043065 | A1 | 2/2009 | Khabashesku et al. | |
| 2009/0087816 | A1* | 4/2009 | Bornstein | A61C 1/0046 433/29 |
| 2010/0015576 | A1* | 1/2010 | Altshuler | A61B 5/0088 433/226 |
| 2010/0312312 | A1* | 12/2010 | Jones | A61P 9/10 424/178.1 |
| 2011/0217665 | A1* | 9/2011 | Walsh | G02B 6/262 600/478 |
| 2012/0245506 | A1 | 9/2012 | Piergallini et al. | |
| 2013/0123642 | A1 | 5/2013 | Yamaguchi et al. | |
| 2015/0032190 | A1* | 1/2015 | Acker | B29D 11/00663 362/558 |
| 2018/0099063 | A1 | 4/2018 | Lyons et al. | |

OTHER PUBLICATIONS

Bartusik, D. et al.; Generating Singlet Oxygen Bubbles: A New Mechanism for Gas-Liquid Oxidations in Water; Langmuir; Jan. 20, 2012; pp. 3053-3060; vol. 28; ACS Publications.

Aebisher, D. et al.; Superhydrophobic Photosensitizers. Mechanistic Studies of 1O2 Generation in the Plastron and Solid/Liquid Droplet Interface; JACS; Dec. 2, 2013; pp. 18990-18998; vol. 135; ACS Publications.

Zhao, Y. et al.; Singlet Oxygen Generation on Porous Superhydrophobic Surfaces: Effect of Gas Flow and Sensitizer Wetting on Trapping Efficiency; The Journal of Physical Chemistry; Jun. 2, 2014; pp. 10364-10371; vol. 118; ACS Publications.

* cited by examiner

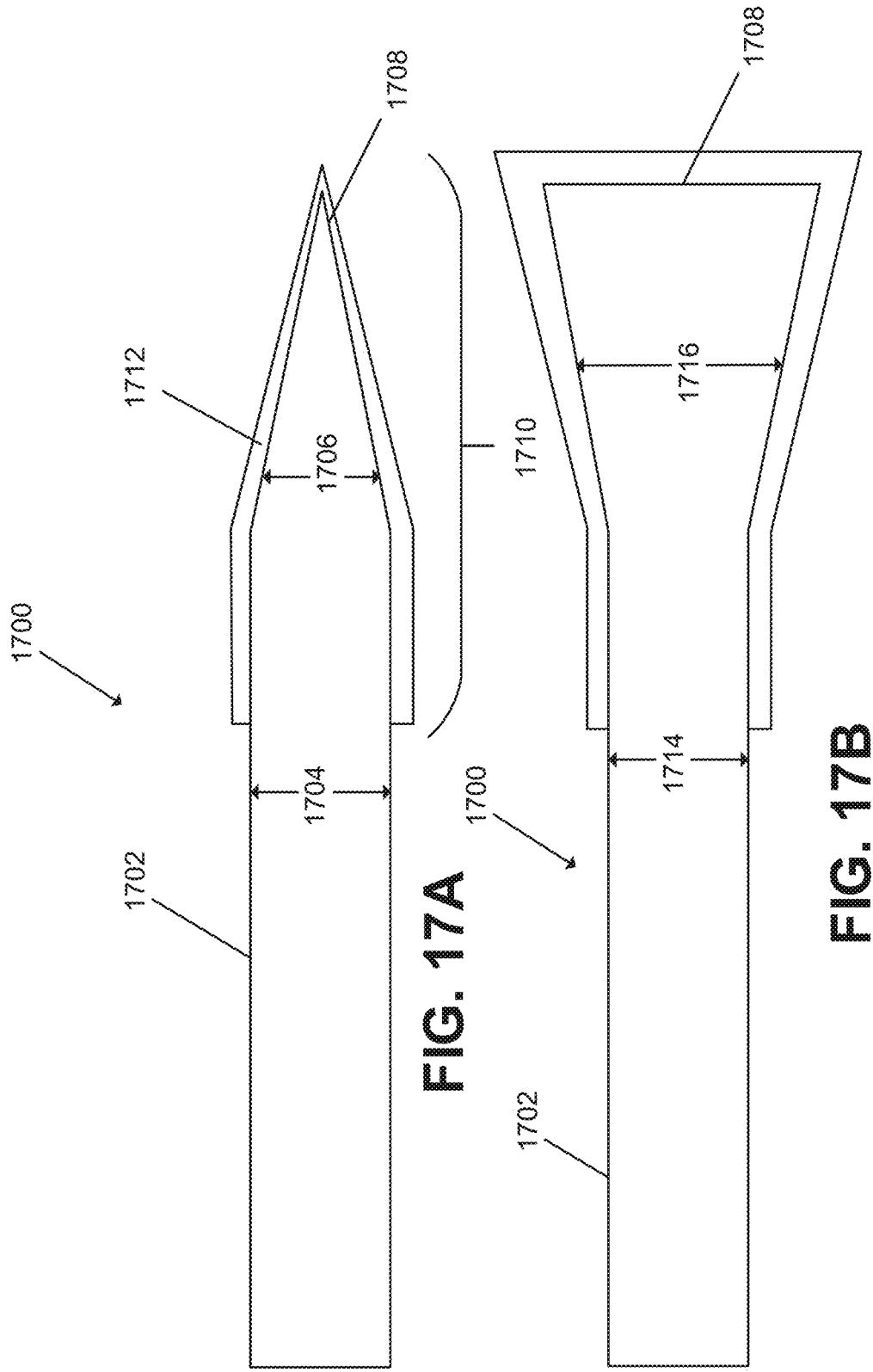

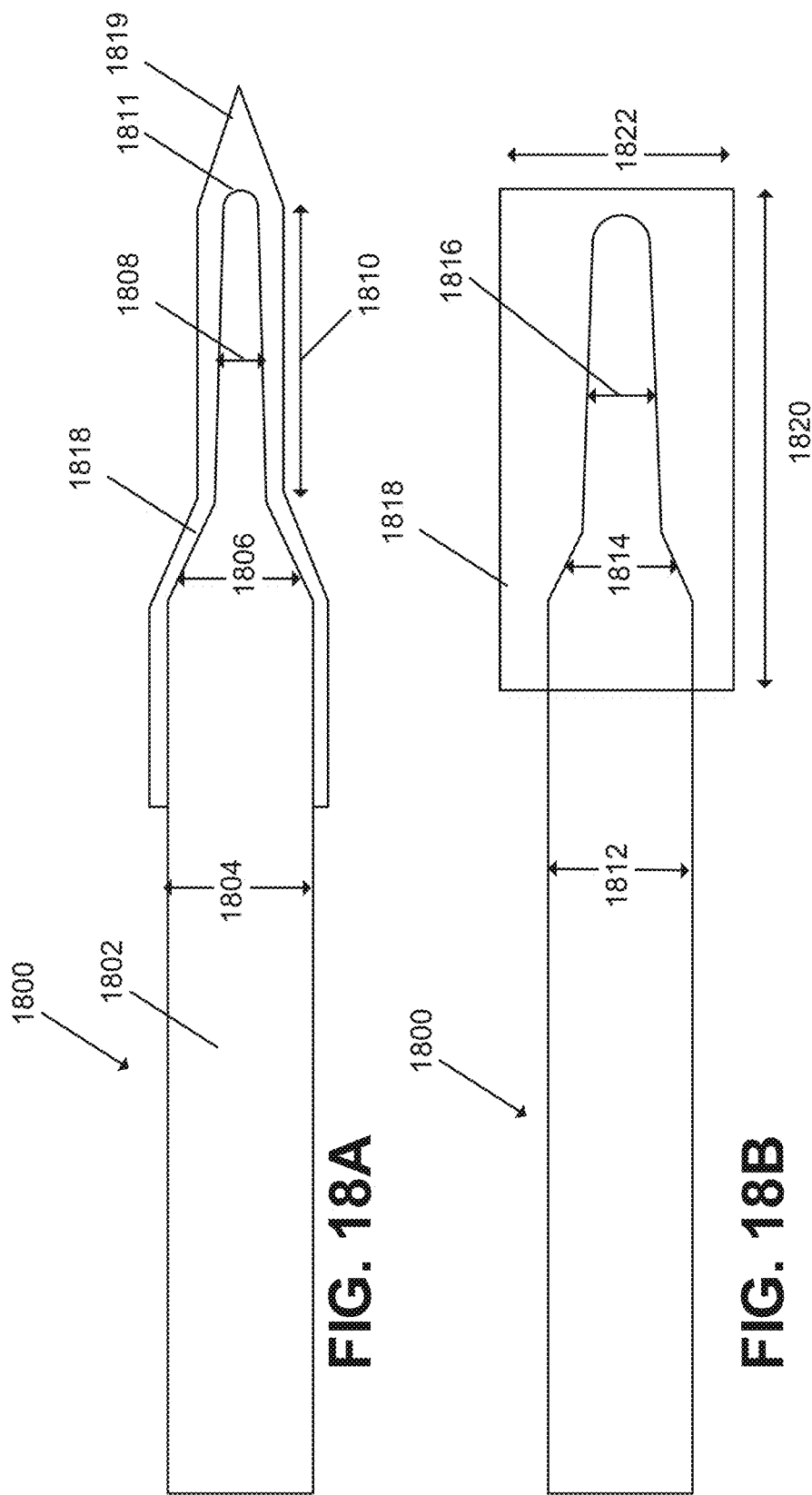

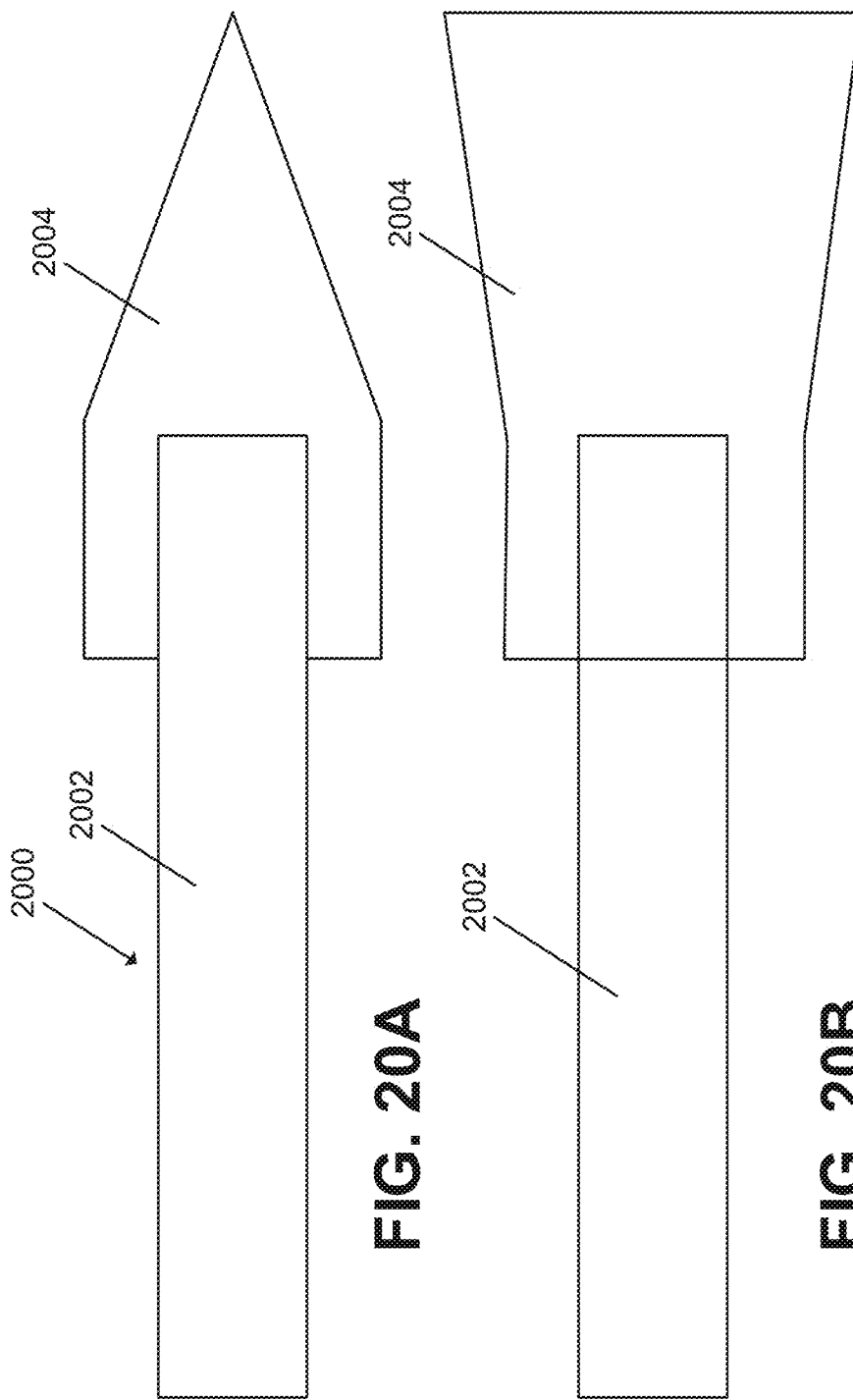

SINGLET OXYGEN GENERATING DEVICE FOR SELECTIVE DESTRUCTION OF PATHOGENS

CROSS-REFERENCE TO RELATED APPLICATIONS

This application claims priority to and is continuation-in-part of U.S. patent application Ser. No. 15/729,005 (filed Oct. 10, 2017) which is a non-provisional of U.S. Patent Application 62/405,583 (filed Oct. 7, 2016), the entirety of which are incorporated herein by reference.

BACKGROUND OF THE INVENTION

The subject matter disclosed herein relates to the use of singlet oxygen to kill cells such as pathogens, bacteria and/or cancer cells. Pathogens and undesirable tissues (e.g. cancer cells) pose a significant risk to human health. A variety of treatment methods are available to destroy these pathogens but none has proven to be entirely successful. Often the cytotoxicity of the treatment agent inappropriately destroys surrounding tissue or is otherwise not sufficiently selective or the treatment agent is persistent thereby allowing pathogens to develop resistance to the agent. An improved method for the selective destruction of pathogens is therefore desirable. The discussion above is merely provided for general background information and is not intended to be used as an aid in determining the scope of the claimed subject matter.

BRIEF DESCRIPTION OF THE INVENTION

A device for generating singlet oxygen is provided. The device has elongated posts extending from a surface, the lateral sides of which have particles with a sensitizer that converts triplet oxygen to single oxygen upon exposure to light. An optical fiber conveys light to the sensitizer and a gas supply tube conveys oxygen to the sensitizer. The device is configured to keep the sensitizer from contacting external fluids, such as saliva.

In a first embodiment, a device for generating singlet oxygen is provided. The device comprises a hand-piece comprising a conical tip at a terminus of the hand-piece; a gas supply tube that conveys oxygen to the conical tip; an optical fiber that conveys light to the conical tip. The conical tip is detachable from the hand-piece and comprises: a cylindrical substrate with an internal surface that is at least partially coated with particles that comprise a sensitizer, wherein the sensitizer converts triplet oxygen to singlet oxygen upon exposure to light; the optical fiber conveys light to the sensitizer; the gas supply tube is disposed upstream of the sensitizer such that oxygen is conveyed to the sensitizer; at least one opening disposed downstream of the sensitizer that directs singlet oxygen to a treatment site; and a hydrophobic barrier that separates the sensitizer particles from the opening, thereby protecting the sensitizer from contacting an external fluid.

In a second embodiment, a method for treating a periodontal pocket of a patient with singlet oxygen is provided. The method comprises conveying a gas comprising triplet oxygen through a hand-piece, the hand-piece comprising a conical tip at a terminus of the hand-piece; a gas supply tube that conveys oxygen to the conical tip; an optical fiber that conveys light to the conical tip. The conical tip is detachable from the hand-piece and comprises a cylindrical substrate with an internal surface that is at least partially coated with particles that comprise a sensitizer, wherein the sensitizer converts the triplet oxygen to singlet oxygen upon exposure to light; the optical fiber conveys light to the sensitizer; the gas supply tube is disposed upstream of the sensitizer such that oxygen is conveyed to the sensitizer; at least one opening disposed downstream of the sensitizer that directs singlet oxygen to a treatment site; a hydrophobic barrier that separates the sensitizer particles from the opening, thereby protecting the sensitizer from contacting an external fluid. The method further comprises inserting the opening of the conical tip into the periodontal pocket of the patient such that the opening is proximate the treatment site; actuating a light source that provides light to the optical fiber, thereby converting the triplet oxygen to the singlet oxygen using the sensitizer; and permitting the singlet oxygen to flow from the sensitizer to the opening and then to the treatment site, thereby treating the periodontal pocket of the patient with the singlet oxygen.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 8C depicts one method for producing elongated ridges onto a substrate while

FIG. 17A and FIG. 17B provide a side view and a top view, respectively, of a wedge-shaped assembly for administering singlet oxygen to a periodontal pocket;

FIG. 18A and FIG. 18B provide a side view and a top view, respectively, of an assembly that uses a blunt-tipped optical fiber in conjunction with a superhydrophobic polymer that provides a pointed tip;

FIG. 20A and FIG. 20B provide a side view and a top view, respectively, of an assembly that uses removable a superhydrophobic polymer that connects to an optical fiber.

DETAILED DESCRIPTION OF THE INVENTION

Periodontal infections continue to plague the world's population primarily due to inadequate dental care, increasing rates of diabetes, and tobacco use. Scaling and Root Planing (S&RP) with or without antibiotics suffers from bacterial resistance and recurrent infections. Periowave, a photodynamic therapy (PDT) method has been used, but there is difficulty in treating deep in pockets, requiring multiple visits. Thus, there is a need for treatment strategies that can generate singlet oxygen site-specifically for enhanced bacterial destruction in deep periodontal pockets (up to 10 mm) to combat recurrence. The disclosed superhydrophobic PDT approach is significant because it could be used as a sole therapy or simultaneously with S&RP to reduce or eliminate these problems.

The disclosed device generates singlet oxygen to eradicate bacterial biofilms in pockets 1-10 mm deep during a single visit rather than multiple visits. The system has at least one of the following advantages: (i) singlet oxygen delivery to periodontal pockets where the superhydrophobic surface provides a barrier so the sensitizer does not contact tissue, (ii) precision for limiting near-neighbor effects where bacterial pockets are adjacent to healthy gum tissue, (iii) countering bacteria hypoxia by delivery of oxygen concentrations by the device tip that are sufficient to sustain PDT, and (iv) combining singlet oxygen disinfection with simultaneous photobiomodulation to stimulate healing and relief from inflammation. For a sensitizer to generate singlet oxygen the sensitizer should strongly absorb light. If the periodontal pocket is deep, the tissue can absorb a portion of the light. The disclosed device addresses this concern. Deep periodontal pockets also have little oxygen present. The disclosed device addresses this concern. The lifetime of singlet oxygen is also known to be shorter in liquid environments than in gaseous environments. The disclosed device enhances the time singlet oxygen spends in the gas phase and thus permits deeper tissue penetration. In other embodiments, the device may be used for non-periodontal treatments such as tumor eradication and bacterial killing in stagnating wounds.

Figure 1:
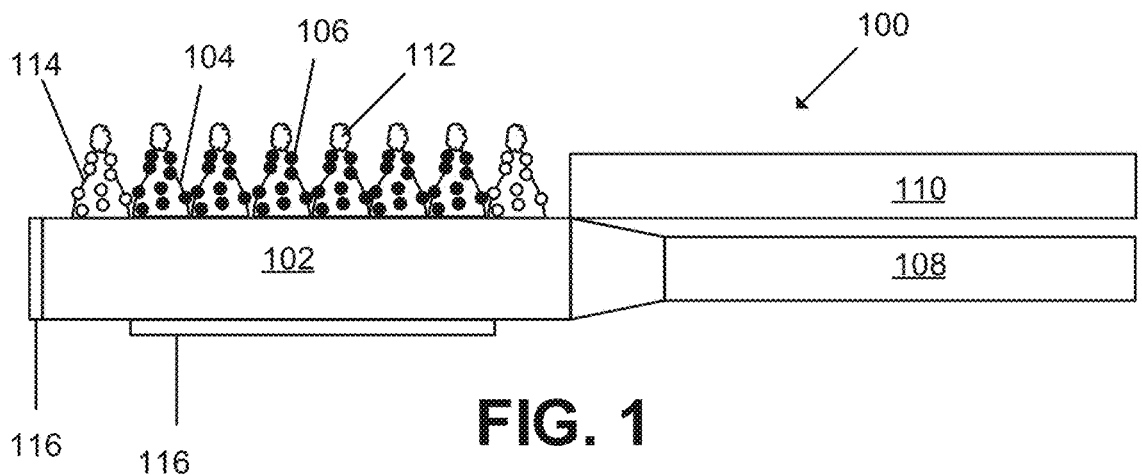
FIG. 1 is a bisected profile view of an assembly for producing singlet oxygen.
Figure 2:
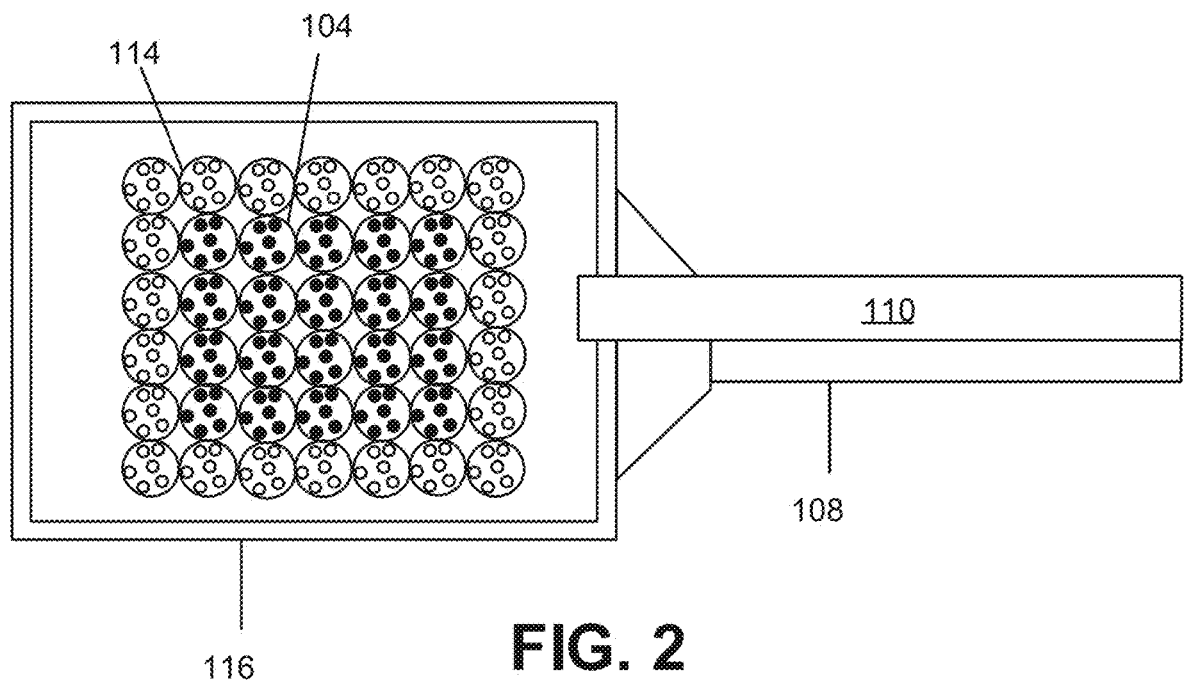
FIG. 2 is a top view of the assembly of FIG. 1.

FIG. 1 depicts an assembly 100 that comprises a substrate 102 with a plurality of elongated posts 104 mounted on a surface thereof. The substrate may be a thin, transparent substrate such a glass, polydimethylsiloxane (PDMS), polymethyl methacrylate (PMMA) or polyethylene terephthalate (PET). In one embodiment, the thickness is between 25 microns and 2 mm. In another embodiment, the thickness is between 25 microns and 500 microns. In yet another embodiment, the thickness is between 25 microns and 250 microns. Each elongated post 104 has sensitizers 106 disposed on at least an external surface of the elongated post 104. The sensitizer is disposed on a lateral surface of the elongated post 104 to prevent external fluids from contacting the sensitizer. The sensitizers 106 generate single oxygen ($^1O_2$) from triplet oxygen ($^3O_2$) upon photoactivation. Such sensitizers are known to those skilled in the art. Examples include porphyrins, phthalocyanines (e.g. Si-phthalocyanine), fullerenes, chlorins, bacteriochlorins, temoporfin (e.g. FOSCAN®) and BODIPY compounds, xanthene and fluorscein dyes (e.g., rose bengal), phenothiazines (e.g., methylene blue), cyanine dyes bearing polymethine chains (e.g., indocyanine green), imides (e.g., naphthalene diimide), polycyclic aromatic hydrocarbons (e.g., naphthalene, anthracene), carbonyl compounds (e.g., benzophenone, fluorenone), nitrogen heterocycles (e.g., acridine, phenazine), sulfur heterocycles (e.g., alpha-terthienyl), coordination compounds (e.g., $Ru(bpy)_3Cl_2$), acenes and phenalenone. There are well-known routes to binding sensitizer to glass. Photoactivation may be accomplished through optical fiber 108 which routes light from a light source to the optically transparent substrate and to the sensitizer particles. In another embodiment, a light emitting diode (LED) is present in the assembly 100 that replaces the need for the optical fiber 108. Mirrors 116, for example, can be used to enhance coupling of light between the substrate 102 and the sensitizer particles. Oxygen can be introduced to the elongated posts 104 using gas supply tube 110. In another embodiment, ambient oxygen is used that replaces the need for the gas supply tube 110. In one embodiment, oxygen is supplied along with an inert gas such as nitrogen or argon. The use of sensitizers on particles disposed on the lateral side of elongated posts provides high surface area contact with gas flow while also providing uniform illumination. For some embodiments, it is desirable to keep the sensitizers 106 away from fluid, such as saliva or other biological fluids. In the embodiment of FIG. 1, this is accomplished by applying inert particles 112 (i.e. sensitizer-free particles) to the top of each elongated post 104. Examples of suitable inert particles include hydrophobic particles, such as silane-treated or Polydimethylsiloxane (PDMS)-treated silica (e.g. CAB-O-SIL®) or polytetrafluoroethylene (PTFE) particles or a food-grade fumed silica (e.g. AEROSIL® 380 F manufactured by Evonik). Additionally, the embodiment of FIG. 1 includes guard posts 114 that circumscribe the elongated posts 104. Elongated posts 104 comprise sensitizers while guard posts 114 comprise inert hydrophobic particles. FIG. 2 provides a top view of the embodiment of FIG. 1 and more clearly illustrates the use of the guard posts 114 to circumscribe the plurality of elongated posts 104. The guard posts 114 repel liquids and thereby protect the elongated posts 104 from such liquids. The guard posts 114 also protect the patient by preventing bodily fluids from contacting the sensitizer. In FIG. 1 and FIG. 2, a mirror 116 is provided to reflect light and enhance the photoactivation of the sensitizer.

The particles serve to increase the surface area of the sensitizer exposed to oxygen. The particles should be small so that the surface area is enhanced. For example, AEROSIL® 380 has a specific surface area of 380 $m^2$ per g with primary particle size of 7 nm. The higher the surface area, the more sensitizer can be loaded and remain available on the surface of the particle to contact both oxygen and light. Alternatively, the particles could be larger, such as 100 nm, 1000 nm (1 micron), 10 microns or 100 microns in diameter. In one embodiment, the particles have a diameter between 10 microns and 100 microns. The larger particles may be advantageous to avoid restrictions due to the use of nanoparticles in contact with human tissue.

The particles can be solid or porous. In some embodiments, porous particles with nanometer or micrometer dimensions are used to further increase the available surface area for sensitizer attachment while persevering the ability of oxygen to diffuse into and out of the particles. Typical porous glass has a specific surface from 10 to 300 $m^2$ per g. By regulating the manufacturing parameters, a porous glass with a pore size of between 0.4 and 1000 nm is produced.

Particles can be made using a sol-gel process where the sensitizer is combined with a glass forming composition (e.g. sol-gel) such that the sensitizer is dispersed throughout the glass. This sol-gel containing a sensitizer can then be ground to a fine power (particle sizes less than 100 microns) and partially embedded into the elongated posts. In one embodiment, the sol-gel is formed such that it becomes porous so that oxygen can diffuse into and out of the micron or nm sized particles and thereby take advantage of sensitizer molecules located both on the surface of the particle as well as the interior of the particle. In one embodiment, the particles consist of the sensitizer.

The particles can be treated to be hydrophobic or hydrophilic. Hydrophobic particles have the advantage that water and bodily fluids are repelled to minimize or prevent liquid-fluid contact. Hydrophobicity can be achieved by several techniques including the use of PDMS, silanes, as well as fluorinating agents (e.g. fluorosilanes).

Synthetic methods can be used to covalently attach sensitizers to native and fluorinated silica particles. For example, a chlorin trimethyl ester can be bound by its ester groups to the OH groups of partially fluorinated silica. Other sensitizer substituents that could be used to bond to silica include halogens, alcohols, amines, carboxylic acids, tosylates, and borates. Nucleophilic substitution chemistry can be used. Other coupling reactions can also be used such as dehydrative carbodiimide "EDC" coupling, NaH chemistry, Sonogashira coupling, Suzuki coupling, click chemistry (e.g., azide-alkyne Huisgen cycloaddition), alkene additions, etc. The sensitizers can also be adsorbed non-covalently over a native silica surface. Sensitizer loading is done to maximize singlet oxygen output.

For example, silica particles (0.4 g) may be soaked in 0.6 M 3,3,4,4,5,5,6,6,6-nonafluorohexyltrimethoxysilane and refluxed in toluene (30 mL) for 24 h, which leads to the replacement of the SiOH groups for the fluorosilane C—H and C—F groups. Any nonafluorohexyltrimethoxysilane that is not covalently attached to the silica surface is washed away by Soxhlet extraction in methanol for 24 h.

A specific example to covalently attach sensitizers to fluorinated silica particles is as follows: chlorin $e_6$ trimethyl ester (0.05 mmol) is reacted with 3-iodopropyltrimethoxysilane (0.25 mmol) and NaH (0.01 mmol) in 5 mL dry THF, and refluxing the mixture at 70° C. for 24 h. The THF is evaporated and leave a residue of chlorin-silane, which is added to 50 mL toluene and 0.4 g silica, and refluxed at 110° C. for 24 h. Chlorin-silane is loaded in 0.17 mmol amounts (99.5% of the SiOH groups) onto silica.

Figure 3:
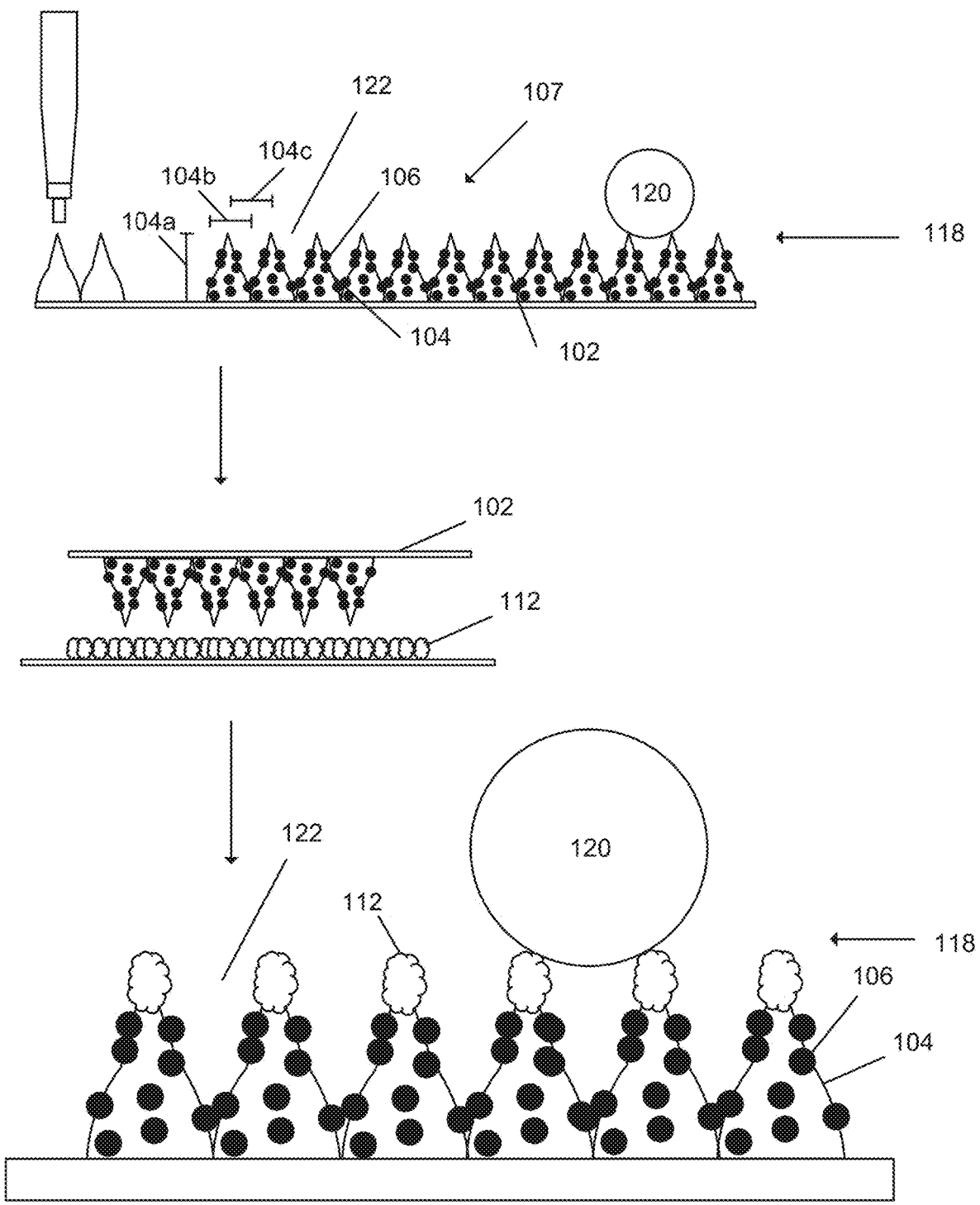
FIG. 3 depicts one method for printing elongated posts onto a substrate.

The elongated posts 104 and the guard posts 114 can be formed using conventional methods such as printing, three-dimensional (3D) printing, molding, and the like. In the embodiment of FIG. 3, a robotic dispensing system is used to print PDMS arrays. Particles (e.g. silica nanoparticles) can be functionalized with the sensitizer and subsequently coated uniformly over the surface of the elongated posts 104. For example, when printing elongated posts using a room temperature vulcanizing (RTC) silicone resin, the elongated posts remain soft and tacky after printing. Particles containing the sensitizer are poured onto this soft, tacky surface such that the post surfaces are at least partially coated. The elongated posts are then cured (either the posts are cured at room temperature for several hours, or the posts are cured at elevated temperature for less time, e.g. 65° C. for 30 minutes). After cure, excess particles are removed by rotating the surface upside down. Blowing clean, dry gas (e.g. air or nitrogen) over the surface further ensures that all particles not bonded to the elongated posts are removed. Another approach would be to dip the elongated post substrate into a bed of the particles. A fluidized bed enables good contact without exerting forces on the uncured elongated posts that could distort their shape. The particles can be located so that they cannot come into direct contact with biofluids and/or tissue. The safety of some sensitizers is not known and so it may be desirable to avoid contact with biological tissue.

The elongated posts 104 have a length 104a, a base width 104b and a pitch 104c. In one embodiment, each elongated post has a base diameter of about 400 microns and taper to a tip diameter of a few microns, a pitch of 500 microns and a height of 900 microns. In one embodiment, the elongated posts are printed on a square array, but could equally well be printed on a hexagonal array, or a circular array—or even a stochastic distribution. Instead of parallel posts, other features could be used as well, for example a series of parallel ridges. The pitch 104c, combined with the surface irregularities from particles 106 produce a hydrophobic barrier 118 in the form of a superhydrophobic surface. A superhydrophobic surface is that surface that exhibit a contact angle of at least 140° (or 150°) with water when tested in accordance with ASTM D7334 08 (2013). An opening 122 permits singlet oxygen to escape. The gas supply tube 110 is disposed upstream of the sensitizer 106 while the opening 122 is disposed downstream of the sensitizer 106. This facilitates the rapid flow of singlet oxygen out of the opening 122 to take advantage of the longer lifetime of singlet oxygen in the gas phase. In one embodiment, the base width 104b is between 300 microns and 500 microns, the pitch is between 400 microns and 600 microns (but is greater than the base width 104b) and the length is between 800 microns and 1000 microns. The tip diameter is between 1 micron and 5 microns.

As shown in FIG. 3, elongated posts 104 may be printed into a surface. The elongated posts 104 may be formed of a polymeric material (e.g. polydimethysiloxane, PDMS) or other suitable material. Other suitable materials include epoxy resins, polyurethane resins, polyester resins, phenol-formaldehyde resins, poly(methyl methacrylate) resins, etc. The elongated posts 104 are then coated with particles comprising the sensitizer 106 to produce assembly 107 which may be used to generate singlet oxygen as described elsewhere in this specification. In another embodiment, after the polymeric material is cured the tips of the elongated posts 104 can be treated with inert particles 112 (e.g. unfunctionalized $SiO_2$ particles). The inert particles 112 further increase the hydrophobicity of hydrophobic barrier 118 to help in repelling fluid 120. The opening 122 permits singlet oxygen to escape. In one embodiment, the guard posts 114 are manufactured by printing new rows of elongated posts either before, or after the sensitizer laden elongated posts are fully cured. The as-printed posts are then coated with particles (for example, hydrophobic silica nanoparticles) using processes described for sensitizer particles described elsewhere in this specification.

Thickness of supporting substrate is selected to be sufficiently stiff so that it can be inserted into a pocket of a biological tissue, thin enough to fit into the pocket without exerting too much pressure on the patient and thick enough to make alignment between the substrate and the light source easy to make and reliable to maintain. In one embodiment the elongated posts have a base diameter of about 400 microns, a height of 900 microns and a concave profile. In some embodiments, the use of smaller diameter and shorter posts is advantageous as that would allow more posts to be in or near the pocket.

Figure 4:
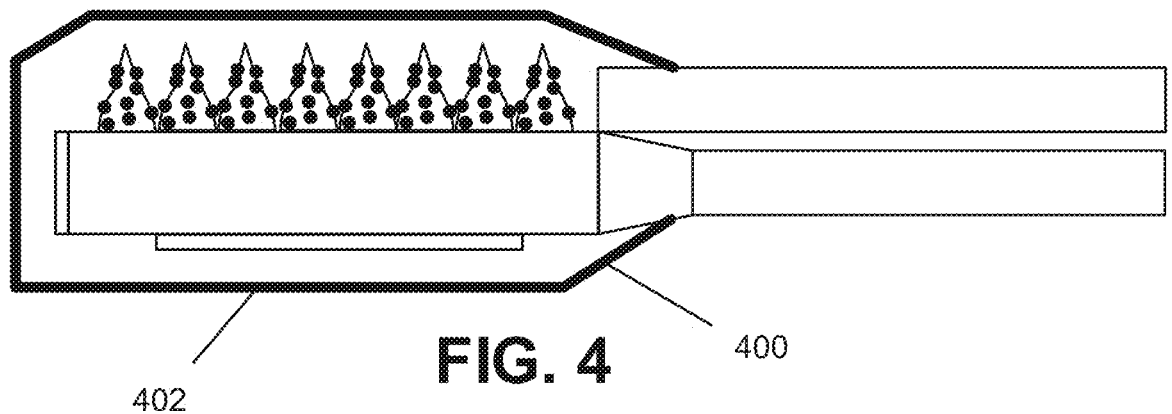
FIG. 4 is a bisected profile view of another assembly that is sealed within a semi-permeable membrane.

FIG. 4 depicts one embodiment that uses a different hydrophobic barrier to protect the sensitizer from surrounding liquids. In the embodiment of FIG. 4, the hydrophobic barrier is semi-permeable membrane 400 that includes opening 402 in the form of pores. Due to the inclusion of semi-permeable membrane 400 the embodiment of FIG. 4 omits guard posts. Singlet oxygen can pass through the semi-permeable membrane 400 but liquids cannot pass through the membrane. Semi-permeable membranes include thin membranes with pore diameters of about 0.05 microns. Pores of this dimension in a hydrophobic substrate (e.g. polyethylene) exhibit a capillary pressure sufficiently high (108 psi) to exclude water under all physiologically relevant conditions. Examples include ultrahigh molecular weight polyethylene (UPE) with 0.05 micron pores with a nominal pore area of 85% sold under the tradename SUREVENT®. Some embodiments, not shown, include both a semi-permeable membrane (e.g. semi-permeable membrane 400) and inert particles (e.g. inert particles 112).

Figures 5A, 5B:
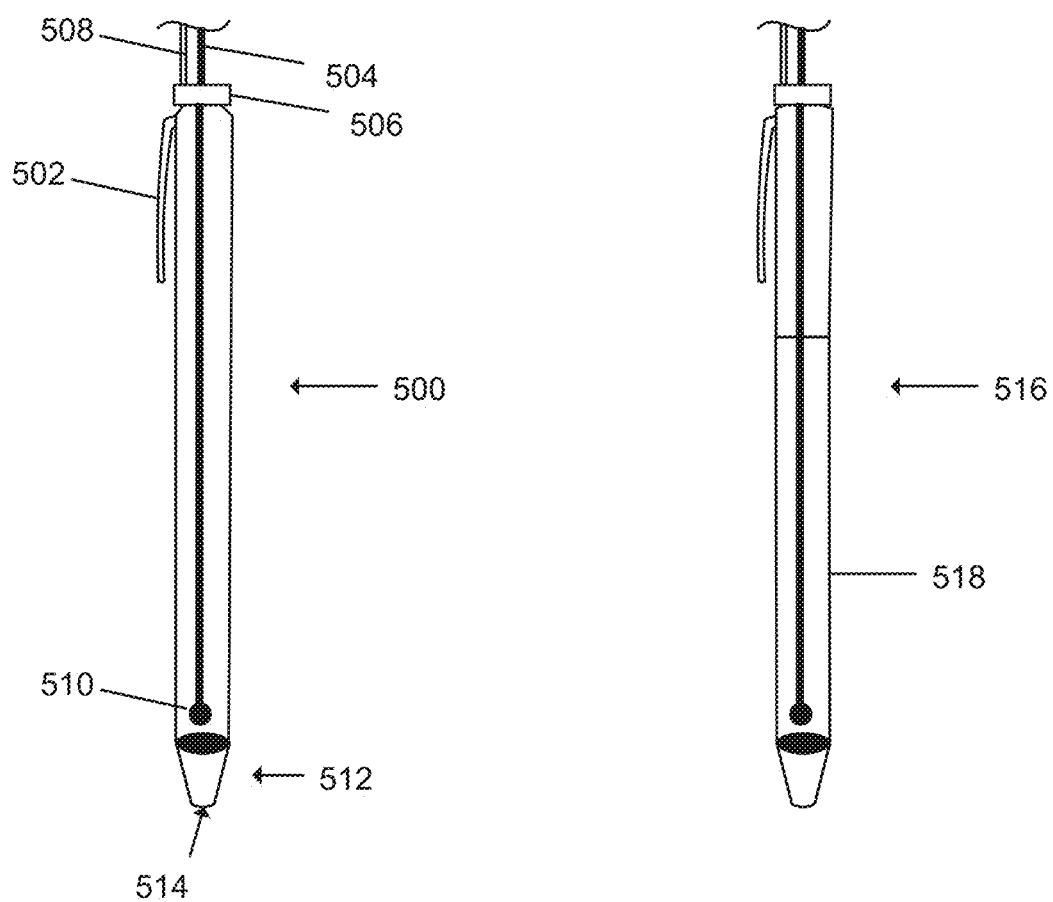
FIG. 5A depicts a hand-piece that generates singlet oxygen using a conical tip.
FIG. 5B depicts a catheter that generates singlet oxygen using a conical tip.

FIG. 5A depicts a pen-like hand-piece 500 that provides a mechanical separation of the sensitizer from the biofluid. A pen-like hand-piece is a cylindrical hand-piece with a length to width ratio of at least 5:1. In one embodiment, the ratio is at least 10:1. Switches 502 allow the user to control the actualization of light from the optical fiber 504. Oxygen flow control 506 controls the rate of flow of oxygen from oxygen supply tube 508. Light from the optical fiber 504 is routed to a lens 510 that can diffuse light over a wide area within the conical tip 512. The conical tip 512 comprises the sensitizer and elongated posts as described elsewhere in this specification. Outlet 514 emits the newly formed singlet oxygen and any residual triplet oxygen. The lifetime of singlet oxygen in the gas phase is known to be less than 100 ms and about 4 µs in aqueous media." An outlet with a 1 mm diameter and a gas flow rate of 0.5 liters per minute causes the gas to flow through the outlet with a velocity of about 8 micro-Liters per ms. Thus singlet oxygen can be generated in the conical tip 512 and conveyed several millimeters before it decays to the ground (inactive) triplet state. The conical tip is removable to facilitate its use as a disposable tip. This permits tips to be used individually for each particular patient to prevent cross-contamination between patients.

FIG. 5B depict a catheter 516. The catheter 516 comprises a disposable sheath 518 that is a relatively stiff support that provides a low-friction exterior. The disposable sheath 518 is sufficiently flexible that it can be pushed into the body. Catheter 516 may have a length to width ratio of at least 10:1. In one embodiment, the ratio is at least 20:1. Examples of catheters including urinary catheters, venous catheters, strength catheters, and the like.

Figure 6:
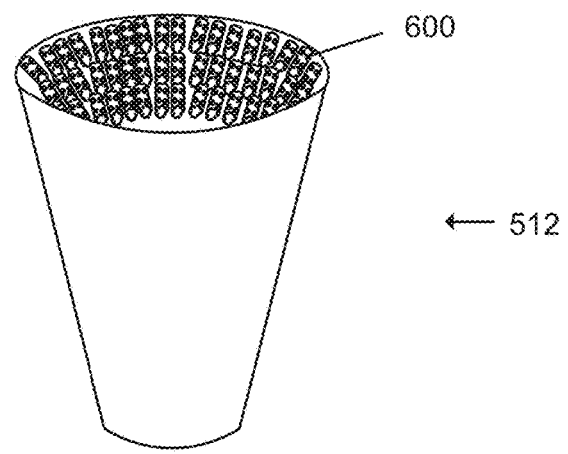
FIG. 6 is a magnified view of a conical tip.

FIG. 6 is a magnified view of an exemplary conical tip 512. The conical tip 512 has a hollow interior whose internal surface is coated with elongated posts 600 which are substantially identical to elongated posts 104. The conical tip 512 may be produced using, for example, the method of FIG. 7.

Figure 7:
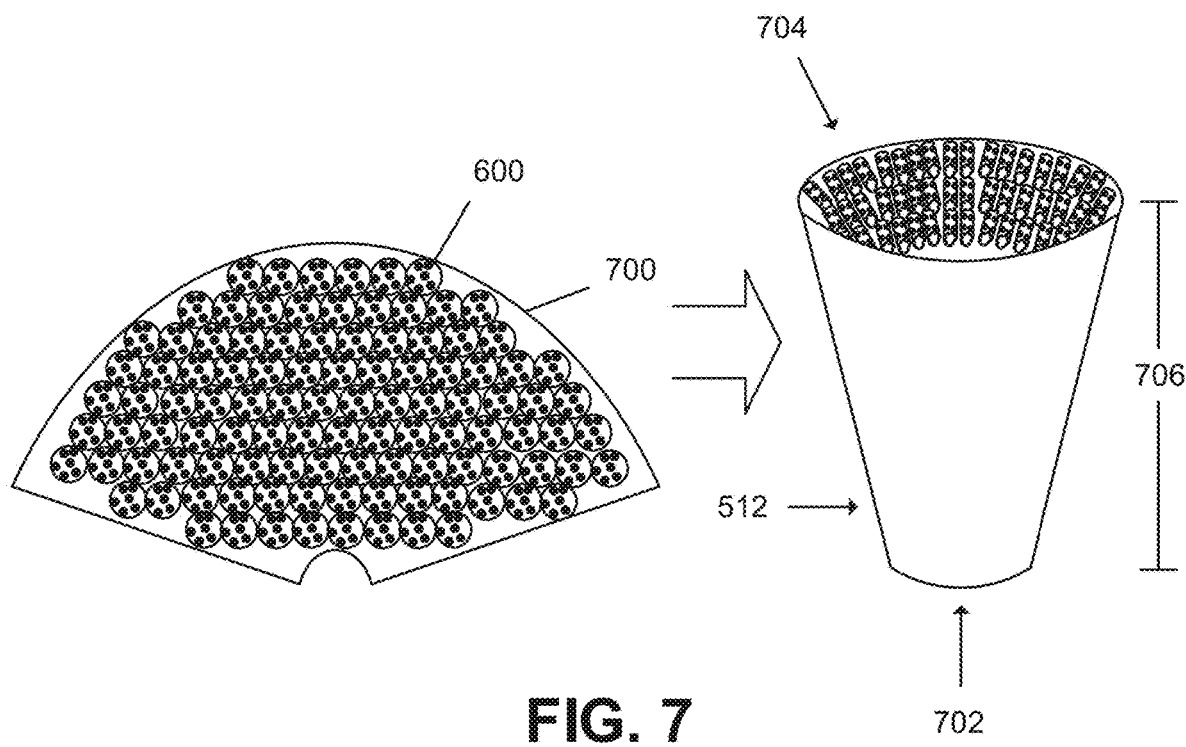
FIG. 7 depicts one method for forming a conical tip.

In FIG. 7, a plurality of elongated posts 600 are applied to a flexible substrate 700. After the sensitizer is applied and the posts 600 are cured the flexible substrate 700 (which is non-permeable) is bent into the conical shape of conical tip 512. The conical tip 512 has a narrow end 702, a wide end 704 and a length 706. In one embodiment, the narrow end 702 has a diameter of about 1 mm, the wide end 704 has a diameter greater than 1 mm but less than 20 mm. The length 706 may be, for example, about 10 mm long.

Figure 8A:
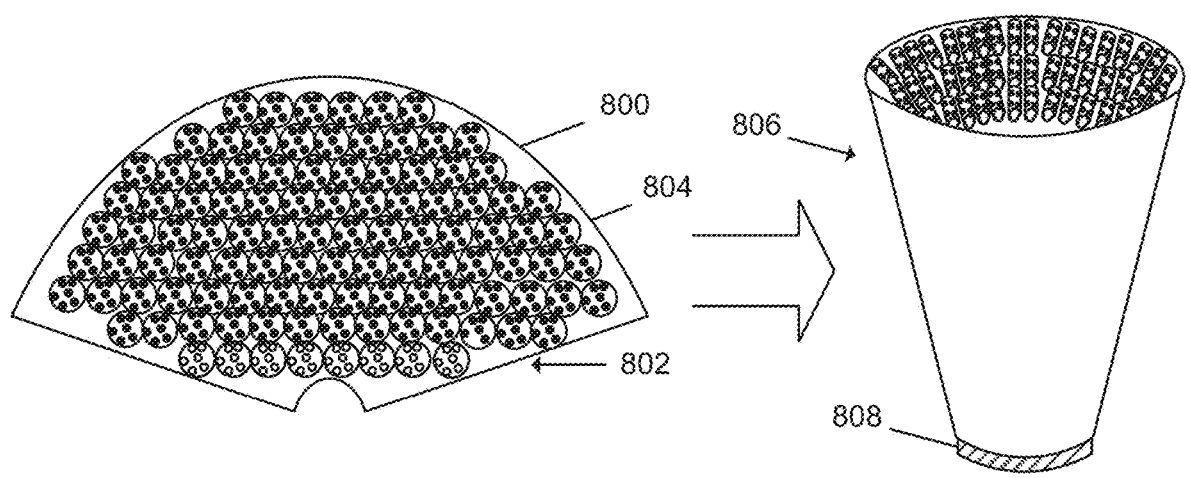
FIG. 8A and FIG. 8B depict two alternative methods for forming a conical tip.

FIG. 8A depicts another method for forming a conical tip 806. A flexible substrate 800 is produced that has both elongated posts 804 with sensitizers and at least one row of guard posts 802. After the sensitizer is applied and the posts 804 are cured the flexible substrate 800 is bent into the conical shape of conical tip 806. A semi-permeable membrane 808 is used to seal the narrow outlet at the narrow end of the conical tip 806. The semi-permeable membrane 808, in combination with the guard posts 802 further protect the elongated posts 804 from contact with biofluids.

Figure 8B:
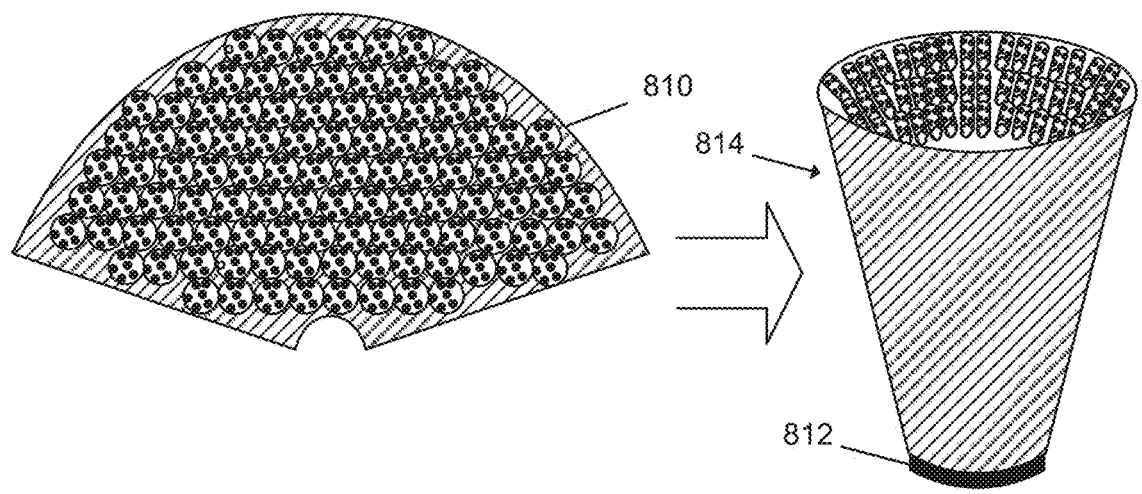

FIG. 8B is similar to FIG. 8A except in that the row of guard posts 802 are omitted, the substrate 810 is a semi-permeable substrate and a non-permeable sealant 812 is used to seal the narrow end of the conical tip 814. The sealant minimizes downward flow of oxygen and promotes the flow of oxygen out of the sides of the conical tip 814 through substrate 810.

Figure 8C:
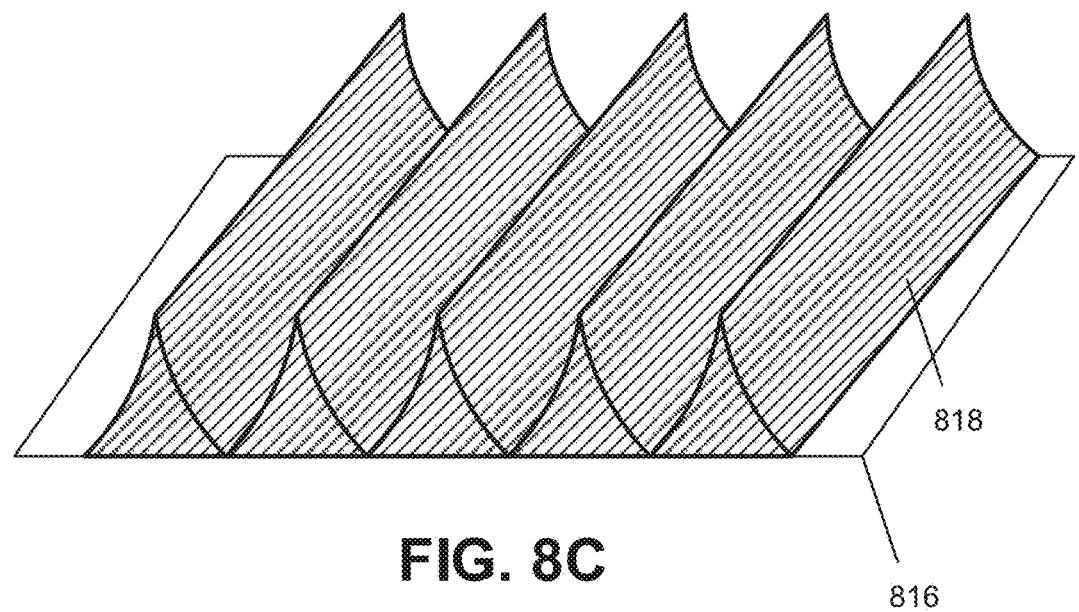
Figure 8D:
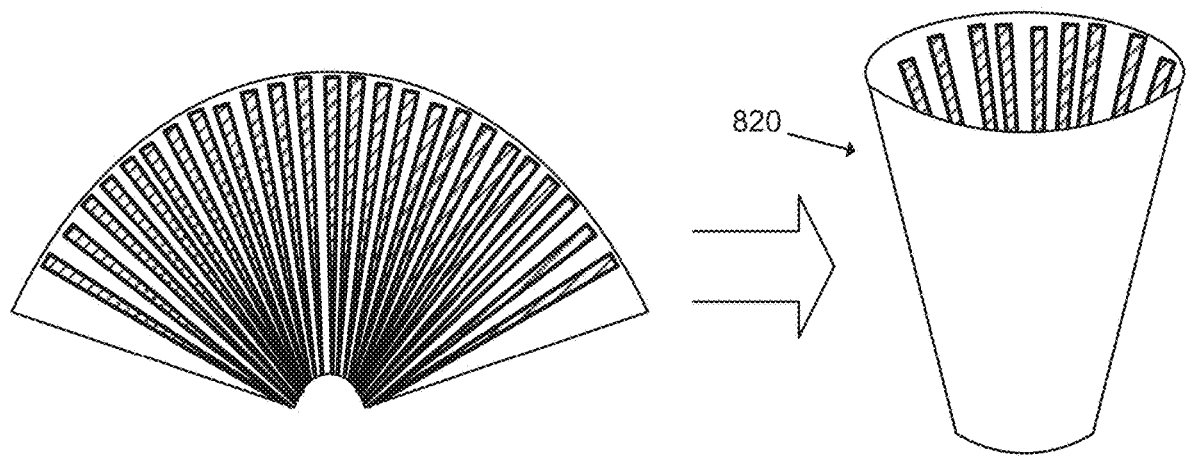
FIG. 8D depicts a method of forming a conical tip.

FIG. 8C depicts an alternative method for forming a hydrophobic barrier. In the embodiment of FIG. 8C the substrate 816 comprises a plurality of elongated ridges 818. Sensitizer can be added to the elongated ridges 818. The elongated ridges 818 define trenches that guide singlet oxygen along the longitudinal axis of the trench. When these trenches are bent into a conical tip 820 (see FIG. 8D) the singlet oxygen is guided toward the outlet of the conical tip.

Figure 9:
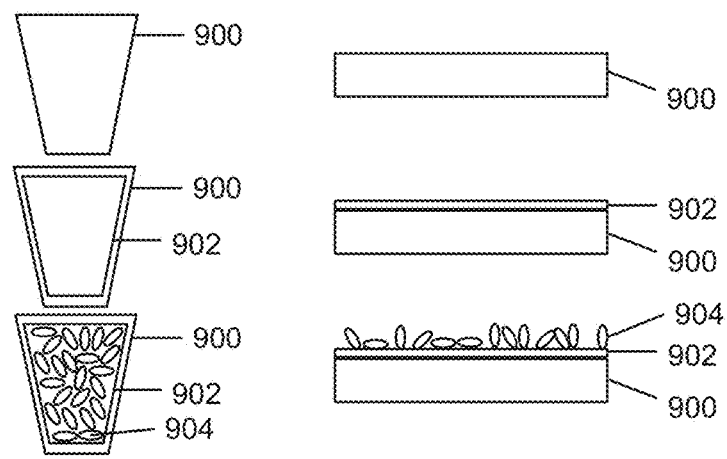
FIG. 9 depicts another method for forming a conical tip.

FIG. 9 depicts another method for forming a conical tip. A flexible substrate 900 is coated with a layer of polymeric material 902. Particles 904 with sensitizer disposed thereon are disposed on the layer of polymeric material 902. The polymeric material is then cured. Because the embodiment of FIG. 9 uses particles 904 rather than elongated posts, the use of a semi-permeable membrane is desirable to keep biofluids from contacting the sensitizer. The available surface area is also reduced (relative to the elongated post embodiment). However, the embodiment of FIG. 9 has other advantages, including cost effectiveness.

Figure 10:
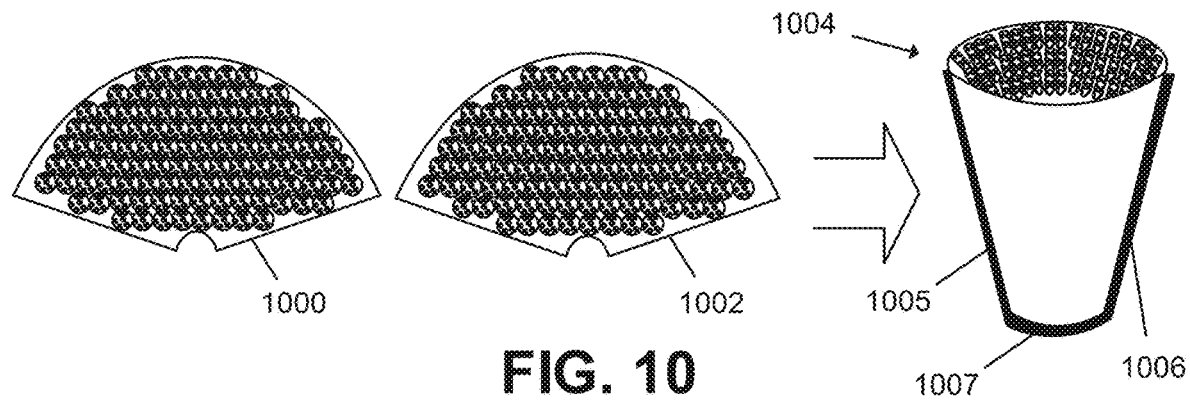
FIG. 10 and FIG. 11 depict two alternative methods for forming a conical tip.

FIG. 10 depicts another method for forming a conical tip. A flexible substrate 1000 (which is a semi-permeable substrate) is coated with sensitizer-containing elongated posts. Likewise a flexible substrate 1002 (which is a non-permeable substrate) is also coated with sensitizer-containing elongated posts. Both of these substrates are bonded together along two long seams 1005 and 1006 as well as along the bottom seam 1007 and bent into a conical shape to form the conical tip 1004. This tip directs the flow of singlet oxygen through only one side of the tip, namely the porous substrate 1000. In this way singlet oxygen would preferentially treat one side of the perio pocket, for example the side facing the tooth, and avoid reacting with the opposite side, for example the side facing the gum. The bonding of 1000 and 1002 can be accomplished with an adhesive, such as PDMS. Alternatively, the two substrates 1000 and 1002 could be heat sealed or ultrasonically sealed if the substrates are fabricated using a thermoplastic substrate such as polyethylene or polyvinylidene fluoride.

Figure 11:
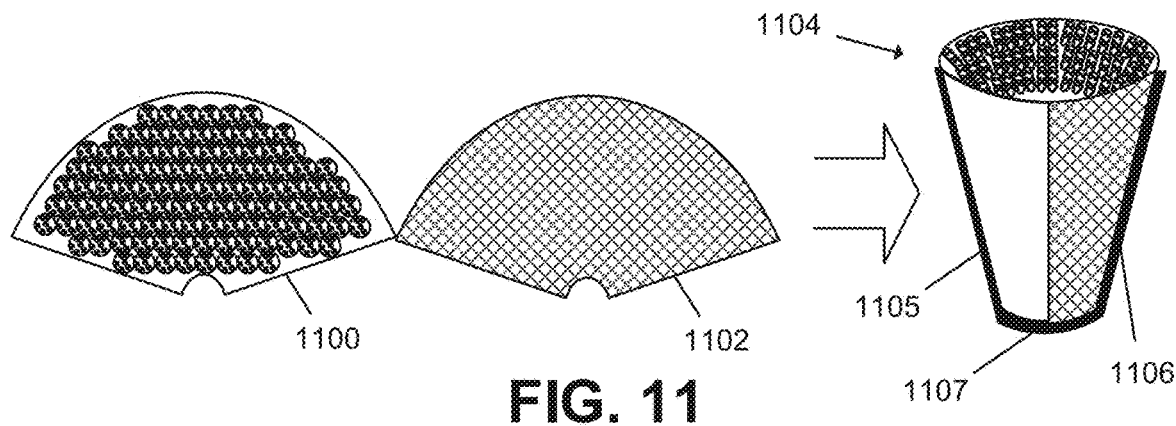

FIG. 11 depicts another method for forming a conical tip. A flexible substrate 1100 (which is a semi-permeable substrate) is coated with sensitizer-containing elongated posts. An optically reflective substrate 1102 is also provided which is flexible. The optically reflective substrate can be a thin metal reflective foil, such as aluminum foil which is approximately 25 microns thick, or it can be a metallized plastic substrate such as vapor deposited aluminum on polyester (Trade Name MYLAR®) where the aluminum thickness is less than 1 micron and the MYLAR® thickness is in the range of 12-150 microns. The two substrates are bonded together to form seams 1105, 1106 and 1107 along the two sides and bottom and bent into a conical shape to form the conical tip 1104. As described elsewhere in this specification, this tip directs the flow of singlet oxygen through only one side of the tip, namely the porous substrate 1100. The reflective substrate 1102 increases the light impinging on sensitizers supported on substrate 1100 and so will increase the quantity of singlet oxygen generated by the device and compensate, in part, for the lower total surface area of sensitizer as compared to, for example, the tip described in FIG. 7. In some embodiments, a second light source is incorporated to provide a second wavelength of light (for the purpose of photobiomodulation) that is reflected off the optically reflective substrate 1102 and exits the conical tip 1104 along with the oxygen. The second wavelength of light may be chosen so that it is not absorbed by the sensitizer thereby increasing the amount of light transmitted as well as preventing heating of the sensitizer which can hasten sensitizer degradation. The substrate 1100 should be chosen so that it does not absorb the second wavelength. The second wavelength is typically in the visible portion of the spectrum and so substrate 1100 could be composed of optically transparent polymers. Many such polymers exist and two examples include polyvinylidene fluoride and polyethylene. The substrate 1100 may appear white due to scattering of light from the rough surface texture and, in some cases, polymer crystals formed in the film. Some light may be scattered back into the tip whereas other light will be scattered in the forward direction and into the tissues of the perio pocket.

Figure 12:
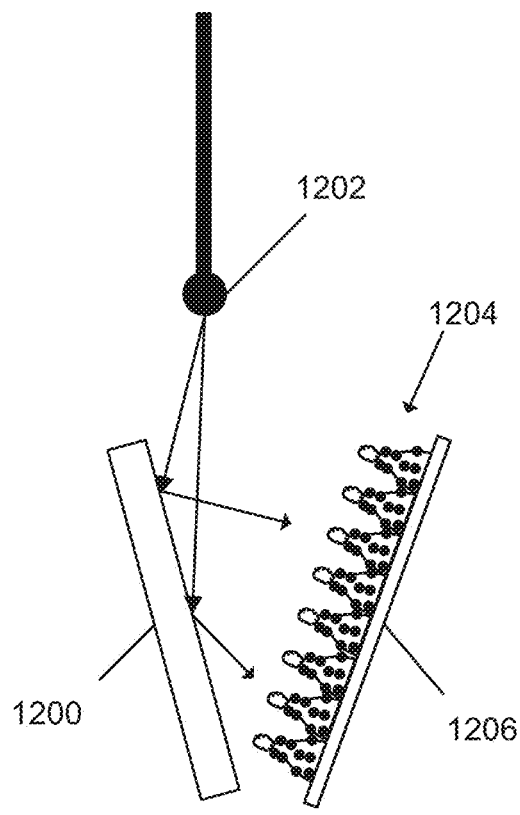
FIG. 12 depicts the use of a reflective substrate to redirect light to promote the generation of singlet oxygen.

FIG. 12 depicts the use of a reflective substrate 1200 to redirect light from a lens 1202 to a plurality of elongated posts 1204. In the embodiment of FIG. 12, the elongated posts 1204 are disposed on a semi-permeable substrate 1206. The substrate can be a reflective metal surface such as aluminum or stainless steel. Alternatively, the reflective substrate could have a thin layer of a reflective metal such as aluminum or silver deposited onto a rigid substrate such as glass or a flexible substrate such as polyester.

Figure 13:
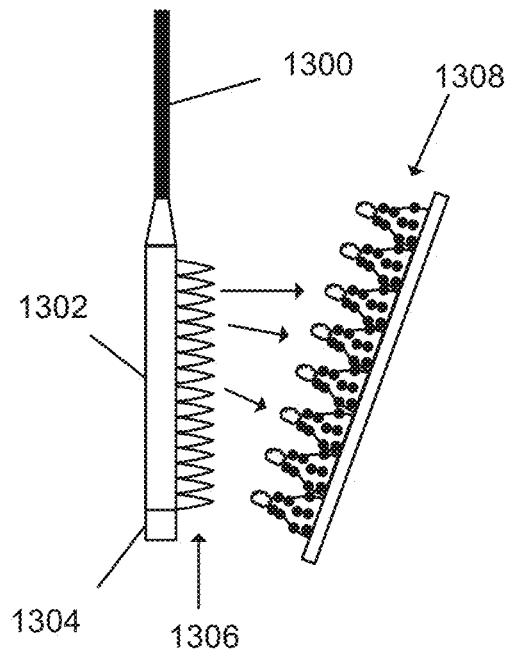
FIG. 13 depicts the use of Frustrated Total Internal Reflection to promote the generation of singlet oxygen.

FIG. 13 depicts an optical fiber 1300 that provides light to a transparent substrate 1302. Transmitted light is reflected by a mirror 1304 to maximize optical efficiency. An array of optically transparent protrusions 1306 are provided to construct a system for Frustrated Total Internal Reflection. This enhances the amount of light that is provided to elongated posts 1308.

Figure 14A:
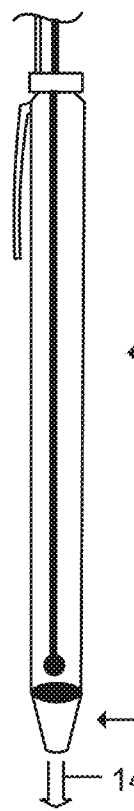
FIG. 14A to FIG. 14D depict a variety of hand-pieces with a variety of conical tips.
Figure 14B:
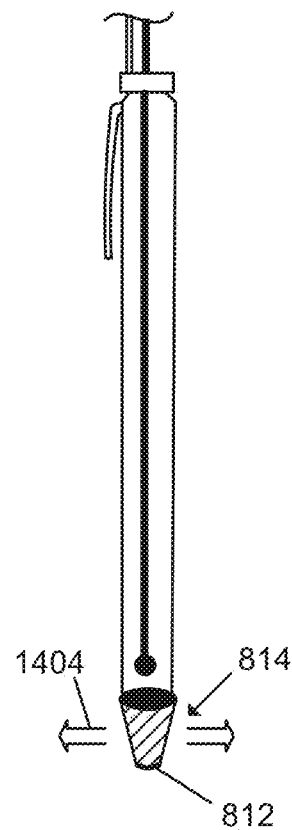
Figure 14C:
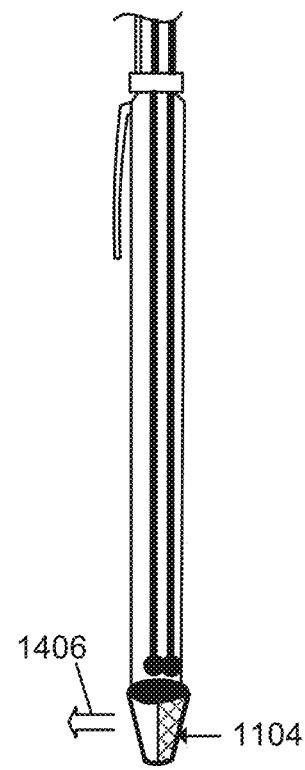
Figure 14D:
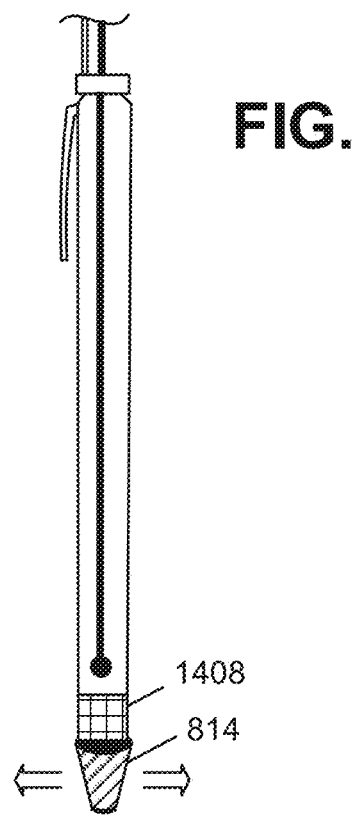

FIG. 14A to FIG. 14D depict various pen-like hand-pieces. FIG. 14A depicts the hand-piece 500 described elsewhere in this specification. The sides of the conical tip 502 are a non-permeable membrane while the narrow end is open. This promotes oxygen flow along downward arrow 1402. FIG. 14B uses the conical tip 814 with a non-permeable sealant 812. The sides of the conical tip 814 is a permeable membrane while the narrow end is closed. This promotes oxygen flow along sideways arrows 1404. FIG. 14C uses the conical tip 1104 with the flexible substrate 1100 (which is porous) and one the optically reflective substrate 1102 (which is non-permeable). This promotes oxygen flow along sideways arrow 1406 through porous surface 1100. FIG. 14D uses a porous glass tip 1408 along the light path. The porous glass tip 1408 is depicted in further detail in FIG. 15A to FIG. 15D. The oxygen flows through the porous glass and exits the end of hand-piece 500 in any direction that has not been sealed to exclude gas flow.

Figure 15A:
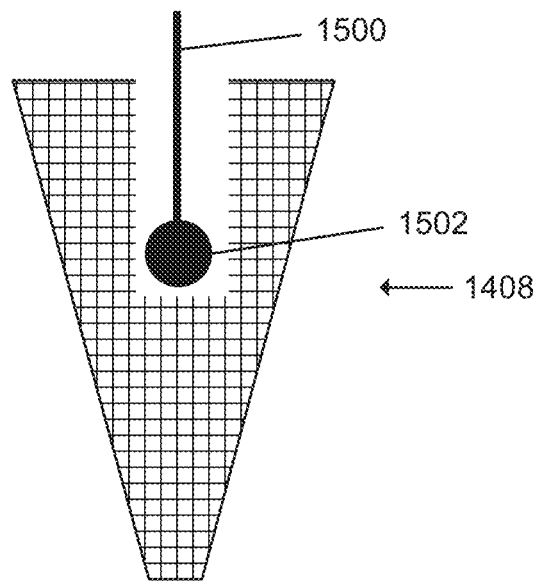
FIG. 15A to FIG. 15D depicts the use of porous glass tip to promote the generation of singlet oxygen.
Figure 15B:
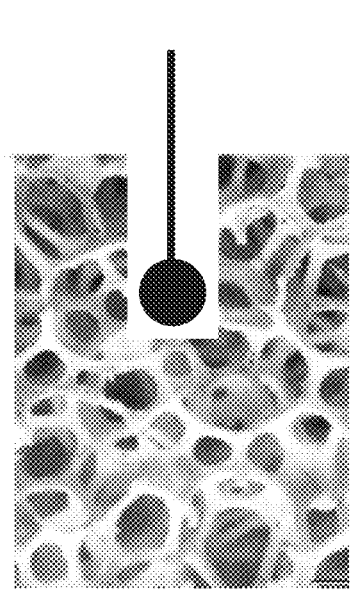
Figure 15C:
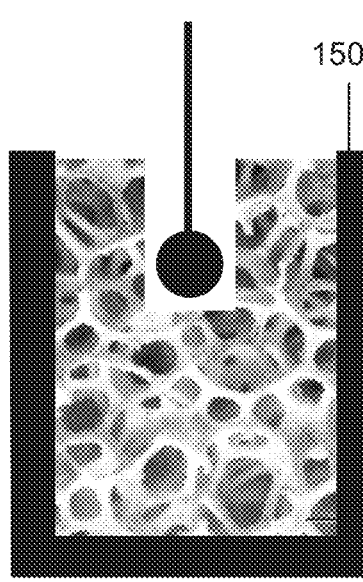
Figure 15D:
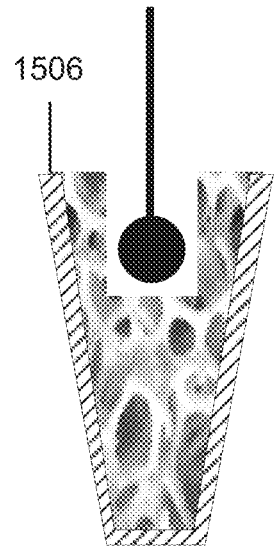

FIG. 15A depicts the porous glass tip 1408. An optical fiber 1500 routes light to lens 1502 that functions as a coupler to spread light through the porous glass tip 1408. The porous glass tip 1408 is embedded/infiltrated with sensitizer. FIG. 15B is an optical image showing the porosity of porous glass. In one embodiment, the porous support comprises a variety of materials including glass, alumina ($Al_2O_3$), other ceramics, or polymers such a polyvinylidene fluoride or polyethylene. In FIG. 15C the surface 1504 of the porous glass is treated to be superhydrophobic. The pores are sufficiently small (e.g. less than 1 micron diameter) to keep water/biofluids from contacting the sensitizer. In one embodiment, the glass surface is treated with fluorosilane to render it superhydrophobic. In another embodiment, the glass surface is coated with PDMS and coated with silica nanoparticles. In another embodiment, the glass surface is treated with a chlorosilane or an alkoxysilane to render it superhydrophobic. In another embodiment, the glass surface is coated with a thin layer of a siloxane polymer such as PDMS. In another embodiment, the glass surface is coated with a thin fluoropolymer by using a commercially available fluoropolymer solution such as TEFLON® AF or Cytop. FIG. 15D shows a semi-permeable membrane 1506 that prevents contact between the sensitizer and biofluids while permitting singlet oxygen to escape. The semi-permeable membrane 1506 can be replaced after each use to avoid cross-contamination between patients. The porous glass tip 1408 can also be removed as needed to avoid cross-contamination and/or to replenish sensitizer as it becomes oxidized.

Figure 16A:
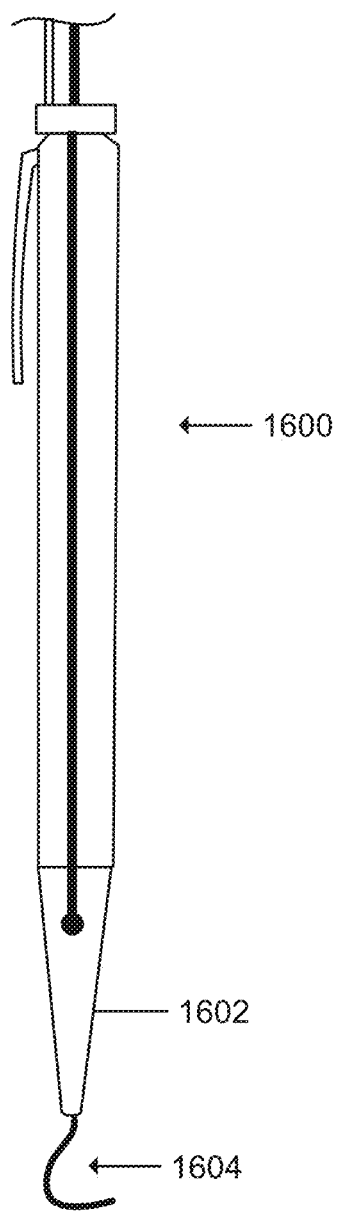
FIG. 16A to FIG. 16C depict a hand-piece that promotes the generation of singlet oxygen wherein the hand-piece uses a variety of scaling tools.
Figure 16B:
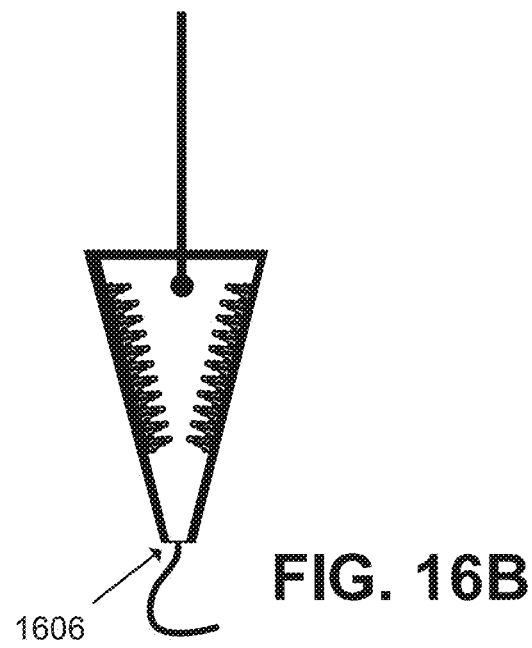
Figure 16C:
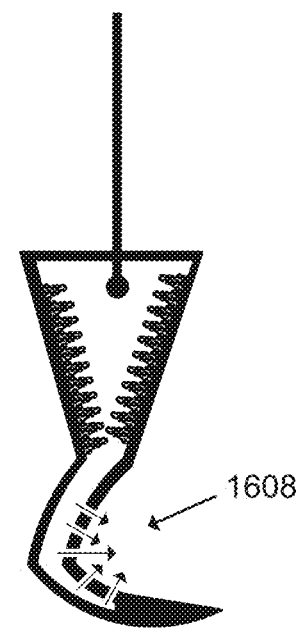

FIG. 16A depicts a combination scaler and PDT device 1600. The conical tip 1602 may be parallel to the scaling tool (not shown) or, as shown in FIG. 16B, the scaling tool 1604 may emanate from the narrow end of the conical tip 1602. The sides of the conical tip 1602 are non-permeable which directs oxygen downward. In one embodiment (see FIG. 16B), an outlet 1606 is provided at the narrow end of the conical tip 1602 and prior to the scaling tool 1604. Oxygen is emitted through the outlet 1606. In another embodiment (see FIG. 16C), the outlet 1606 is omitted and the scaling tool 1602 is hollow. Oxygen is directed out of outlet 1608 in the tip of scaling tool 1602.

Additional Devices for Treating Periodontal Disease

FIG. 17A depicts a side view of an assembly 1700 for treating periodontal disease. The assembly 1700 comprise an optical fiber 1702 with a first height 1704 that narrows to a second height 1706 proximate a terminal point 1708. A terminal portion 1710 of the assembly 1700 is coated with a superhydrophobic polymer 1712 that is optically transparent, biocompatible and comprises sensitizer particles for generating singlet oxygen. In one embodiment, the superhydrophobic polymer 1712 is a layer between 50 and 500 microns thick.

FIG. 17B depicts the assembly 1700 from a top view. The optical fiber 1702 has a first width 1714 that widens to a second width 1716 proximate the terminal point 1708. In this manner the assembly 1700 is provided with a wedge tip. The wedge tip reduces the amount of light that exits the optical fiber 1702 in a direction that is parallel to its longitudinal axis and enhances the amount of light the exits the optical fiber 1702 in directions that are non-parallel to (including perpendicular to) its longitudinal axis.

The use of a wedge tip has been found to significantly increase the power density of the emitted light in directions that are non-parallel to the fiber's longitudinal axia. Two tips were fabricated to illustrate this point. Both tips used a 1 mm optical fiber (POF—Eska CK-40, Poly(methyl methacrylate) PMMA) manufactured by Mitsubishi Chemical Co.). Tip A coated this optical fiber with PDMS (Wacker silpuran 6000/50 made to be superhydrophobic) that was shaped as a rectangle (0.75 mm×6 mm×0.5 mm). Tip B coated this optical fiber with PDMS (same composition as Tip A) that was shaped as a wedge (1 mm×3 mm×0.5 mm). Tip B had ×3.8 more power density (mW/mm$^2$) compared to Tip A at the sides of the optical fiber. Without wishing to be bound to any particular theory, it is believed the wedge shape causes about 90% of the optical power to exit from the sides of the wedge. As used in this specification, the term 'wedge' refers to a shape that changes its height profile to narrow over its length. Examples of wedges include FIG. 17A, FIG. 17B, FIG. 18A, FIG. 18B, FIG. 19A and FIG. 19B.

In one embodiment, roughening of the exterior surface of the superhydrophobic polymer 1712 increases the efficiency of light escaping from the roughened area. This is true for at least two reasons: (1) removal of cladding and increased surface area and (2) creating multiple angles that enable light to escape regardless of the incident angle. The optical fiber may be glass or a polymer optical fiber (POF) that is rigid. This rigid nature permits the terminal portion 1710 to be inserted into periodontal pockets. Examples of suitable polymers include PDMS, FEP, PTFE, and other transparent and hydrophobic coating materials. Such materials are chemically stable, biocompatible and can be made to be superhydrophobic by known techniques.

Figure 17C:
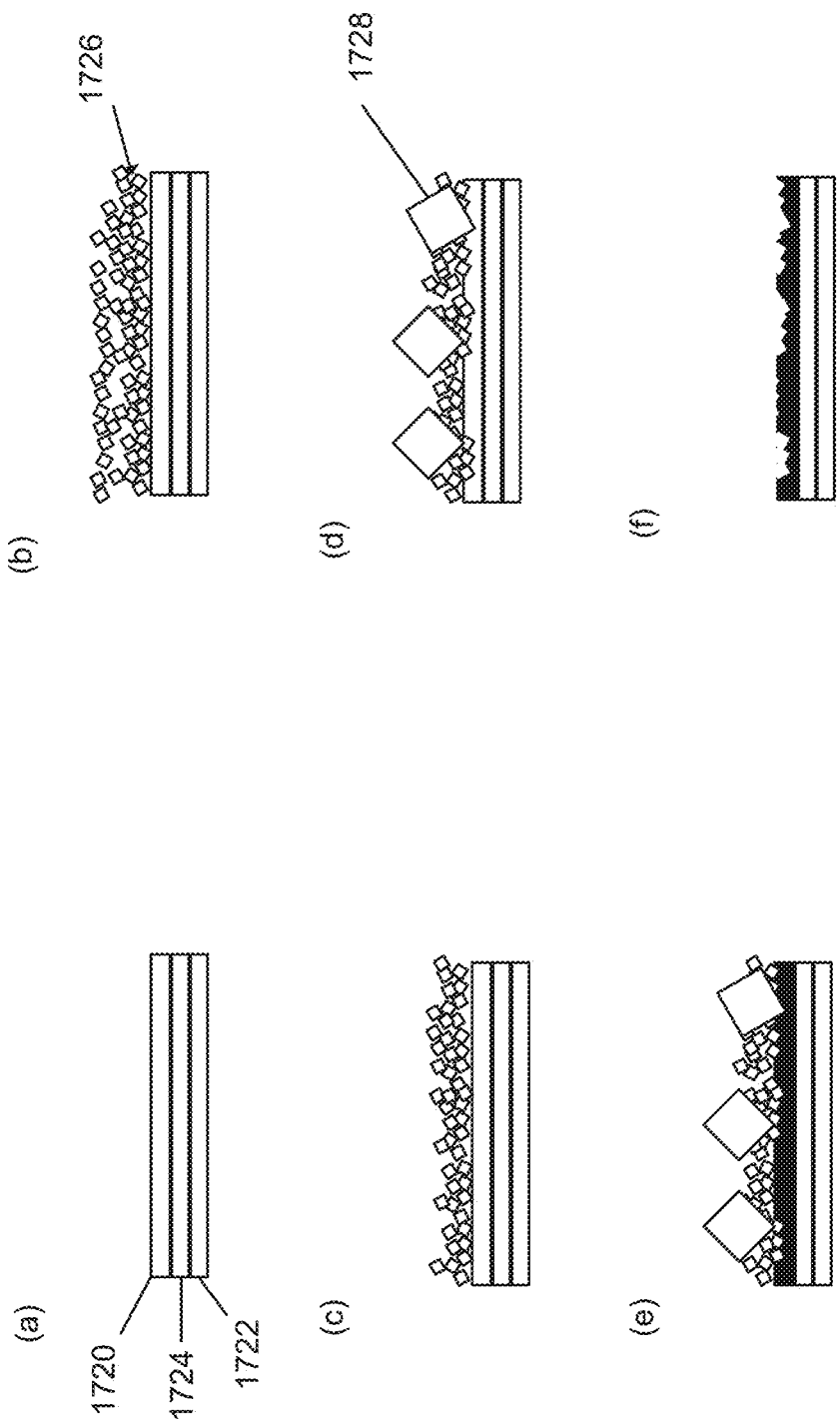
FIG. 17C depicts a method of forming a roughened surface.

In one embodiment, soluble salts are used to produce the roughened surface. Referring to FIG. 17C and panel (a) depicted therein a thermoplastic or thermoset polymer film 1720 is prepared on a flat substrate 1722. A release layer 1724 can be used between the polymer film 1720 and the substrate 1722, if a free-standing polymer film is desired. The polymer film thickness can be 10 microns or larger. The polymer film can be an uncured resin, a thermoplastic polymer above its melting point, or any polymer heated to a temperature where it has a relatively low viscosity. The low viscosity is utilized so that soluble particles (e.g. NaCl) can easily adhere on the surface of the polymer upon impinging with a sufficient force. For thermoplastic polymers, the softness and the tackiness can be adjusted by controlling the temperature of the polymer as well as filler concentration. For thermoset polymers, the softness and tackiness can be adjusted by temperature, molecular weight, small molecule additives, as well as filler concentrations. The polymer should possess intrinsic hydrophobicity, such as PE, PP, silicone, fluoropolymers and others.

Figure 17D:
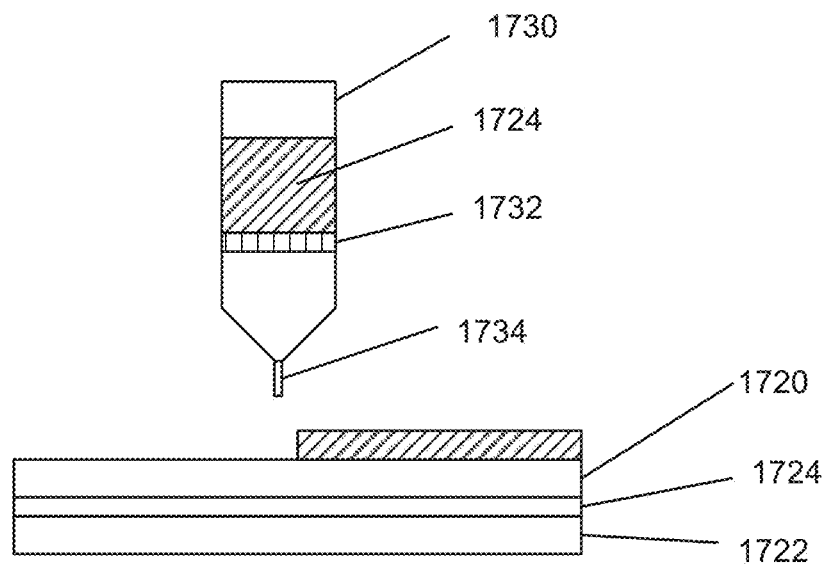
FIG. 17D illustrates an example of equipment for depositing fine salts.

Referring again to FIG. 17C and panel (b) depicted therein, a layer of water-soluble fine salt particles 1726 is formed on the surface of the polymer by causing the salt particles to impinge onto the polymer surface. The velocity of the fine salt particles can be adjusted so that the fine particles can adhere onto the polymer once it touches the polymer matrix. When the softness and tackiness of polymer matrix is optimized, particle adhesion can be achieved simply by allowing the particles to fall a short distance under the influence of gravity. Because the relative humidity of the environment can greatly affect the aggregation of fine salt particles, a sieve with a certain pore size can be used to disperse the fine particles by vibrating, shaking or other mechanical stirring methods. The particles can also be kept dry by operating the dispensing process in a desiccator or dry-box. A dry dispensing system example is shown in FIG. 17D. A fine salt particles container 1730 contains fine salt particles 1726. A mesh 1732 is present that allows particles below a size threshold to be dispensed. For example, the mesh 1732 may be sized to permit particles smaller than 90 microns to be dispensed through a nozzle 1734.

The fine particles deposited on the polymer film are fluffy, i.e. the particle layer is not densely packed. The size of the fine salt particles can be between 10 nm to 100 microns. The shape of the particles can be spheres, cuboid, irregular shapes or a mixture of various shapes and sizes. The distance above the polymer surface where the fine particles are released (from the end of the nozzle to the polymer surface) can be 0.2 mm or higher. The thickness of the fluffy fine particles can be larger than 100 microns. The fine salt particles can be any water-soluble salt. Examples include: NaCl, $CaCO_3$, $NaHCO_3$, KCl, $CaCl_2$, $MgCl_2$, $Na_2SO_4$, sugar, acetylsalicylic acid, and polyvinyl alcohol particles. Particles soluble in organic solvents, such as ethanol or tetrachloroethylene, could also be used provided the solvents do not dissolve the polymer. Such particles that dissolve in organic solvents include waxes and polystyrene particles. In addition, ice particles may be used provided the processing temperatures are below the freezing point of water.

Referring again to FIG. 17C and panel (c) the fine salt particles that are loosely bound are removed from the polymer surface by gently shaking, vibrating or tapping the carrier substrate with the salt particles facing down, resulting in a thin layer of fine particles randomly distributed over the entire polymer surface.

Figure 17E:
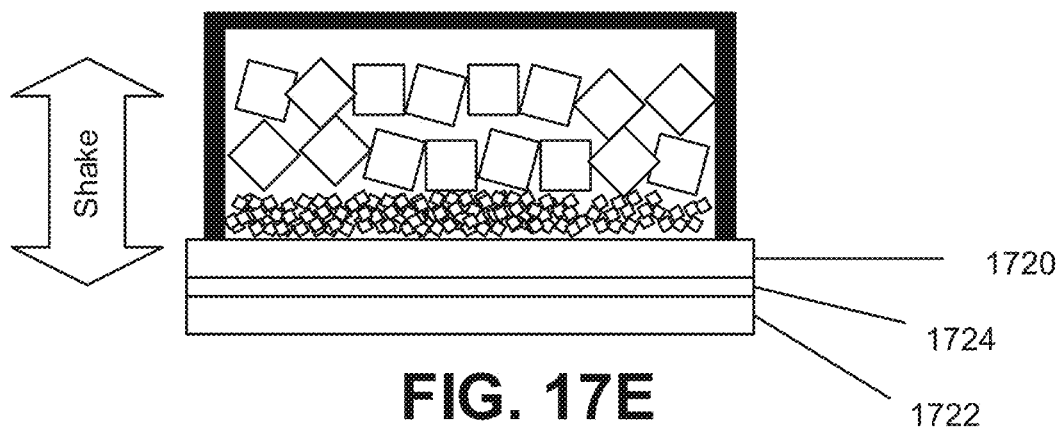
FIG. 17E schematically illustrates a shaking method to apply coarse salt on a surface previously coated with fine salt.

In FIG. 17C, panel (d) a layer of coarse salt particles (e.g. 100 microns to 3 mm diameter) are impinged onto the polymer film by (1) adding coarse salt particles 1728 and (2) shaking/vibrating as shown in FIG. 17E. A container can be used to store coarse salt particles, and the polymer coated with the fine salt particles can be secured to the bottom of the container. The whole system including the container, the polymer film coated with fine salt particles and the coarse particles can be shaken and/or vibrated under controlled conditions (e.g. a certain energy input) so that the fine salt particles are forced deeper into the polymer film. During the impact of coarse salt particles, a larger scale of surface roughness can be generated on the polymer surface.

Excessive vibrational energy input during the coarse salt particle impingement step can cause the fine salt particles to become fully embedded into the polymer matrix. Fully embedding the salt particles will make the particles difficult to remove during the dissolution step and so may leave residual salt particles within the bulk of the polymer and/or porous voids that reduce the mechanical properties of the polymer. Moreover, the formation of micro-scale and nano-scale fine structures on the polymer surface may not develop properly if particles are full embedded, reducing the superhydrophobic properties of the polymer surface.

Referring again to FIG. 17C, panel (e) the polymer film is solidified by cooling to room temperature for thermoplastic polymers or crosslinked at elevated temperatures for thermoset polymers. Solidification can also occur for some thermosetting polymers by exposing the material to room temperature for extended periods of time (e.g. room-temperature vulcanizing silicone elastomers). Other systems that can be cured at room temperature, or below room temperature, are UV light crosslinking systems. Such polymers include UV-curable silicones (e.g. SILOPREN® UV curing systems from Momentive).

In FIG. 17C, panel (f) the salt particles are removed by dissolution with the appropriate solvent and the surface is dried to exposure the micro/nanostructures. Heating can be used to increase the particle dissolution rate. The time required to ensure complete removal of all soluble particles will depend on several variables including particle size and energy imparted during impingement. In some cases, dissolution may take only 1 minute or less. In other cases, several hours may be required. For certain applications, it may be sufficient to remove only a fraction of the soluble particles to reduce the time required and thus lower costs. For example, in some cases, it may be sufficient to remove 75%, 85% or 95% of the soluble particles and still maintain the desired roughness. In some other cases, it may be preferred to dissolve only a fraction of the particles, leaving a percentage of the particles embedded in the surface. For example, if the device is designed to increase the pH of an acidic system which it contacts, then $CaCO_3$ particles may be used to create the surface topography. By leaving a small fraction of $CaCO_3$ particles embedded in or near the surface, the residual $CaCO_3$ particles will react with the acid and increase the pH of the system. The surface is dried by exposure to a stream of compressed air or by heating methods before use.

In the preceding description the terms "soluble particles" and "salt particles" were used interchangeably. Salt particles of NaCl are used in the following example, but any readily soluble particle could be used including $CaCO_3$, sucrose, etc. Particles other than NaCl may be advantageous. Because NaCl typically crystallizes in a cubic morphology, particles that crystalize in less symmetric morphologies (e.g. rhombohedral or rod-like morphologies) may impart a greater degree of surface roughness leading to a superhydrophobic surface that is more stable against transitioning from the Cassie state to the Wenzel state, and/or that can exhibit greater droplet mobility (i.e. a lower contact angle hysteresis). An advantage of the process described herein is that the micro-scale and nano-scale features created by the dissolution of the salt particle are observed only on the surface of the polymer coating. The salt particles do not become fully embedded within the polymer matrix. Thus the superhydrophobic surface contains neither residual salt particles, nor any pores fully encapsulated within the polymer that would lower the density of mechanical strength of the polymer.

Table 1 provides data concerning five different PDMS surfaces that were roughed under various conditions. Without wishing to be bound to any particular theory, the use of indentations with a small diameter (e.g. 1-20 microns) in combination with indentations with a large diameter (e.g. 40-300 microns) is believed to produce the observed superhydrophobic properties of the surface.

| 1 | Fine salt | 2 μm | 1-18 μm | 136 ± 5 | N/A | RMS = 1.7 μm by AFM |
|---|---|---|---|---|---|---|
| 2 | Coarse salt | 120 μm | 40-280 μm | 129 ± 4 | 54, 63 | Only large pores |
| 3 | Fine salt + static coarse salt | 3 μm | 2-13 μm | 151 ± 2 | N/A | Only small pores |
| 4 | Fine salt + mechanically shaken coarse salt | 10 μm | 2-340 μm | 152 ± 2 | 26, 62 | Small and large pores |
| 5 | Fine salt + hand shaken coarse salt | 4 μm | 2-19 μm | 154 ± 4 | 48, 50 | Small and large pores plus protruding features |

In use, the assembly is inserted into a periodontal pocket. Light is provided to the optical fiber which, in turn, activates the sensitizer. The sensitizer produces singlet oxygen from the ambient oxygen. Without wishing to be bound to any particular theory, the superhydrophobic surface is believed to trap ambient oxygen near the sensitizer surface which increases singlet oxygen production. The wedge shape of assembly 1700 allows at least three distinct areas to be treated simultaneously to ensure eradication of harmful bacteria from the periodontal pocket. First, a first surface of the wedge contacts and treats the tooth surface (i.e. the enamel and cementum covering the root of the tooth). Second, a second surface of the wedge (opposite the first surface) contacts and treats the gum surface (i.e. the soft gingiva tissue that normally contacts the tooth as well as any exposed periodontal ligaments). Third, the tip of the wedge treats the bottom of the periodontal pocket where the gingiva and connective tissues attach to the enamel or cementum of the tooth. The angle of the wedge controls the relative distribution of light illumination, and thus the singlet oxygen dose administered to each of these three surfaces. In one embodiment, the assembly is angled to provide uniform dose to all three surfaces. In another embodiment, the assembly provides a minimal light dose (e.g. less than 20% of total light, measured in Joules per square centimeter) to the bottom area while providing an increased dose to the two wedge surfaces (e.g. more than 80% of total light). In one embodiment, the assembly provides more than 80% of total light to the first surface (the tooth surface). In yet another embodiment, the assembly provides the same light intensity to all three surfaces (e.g. about one third of total light to each).

Figure 17F:
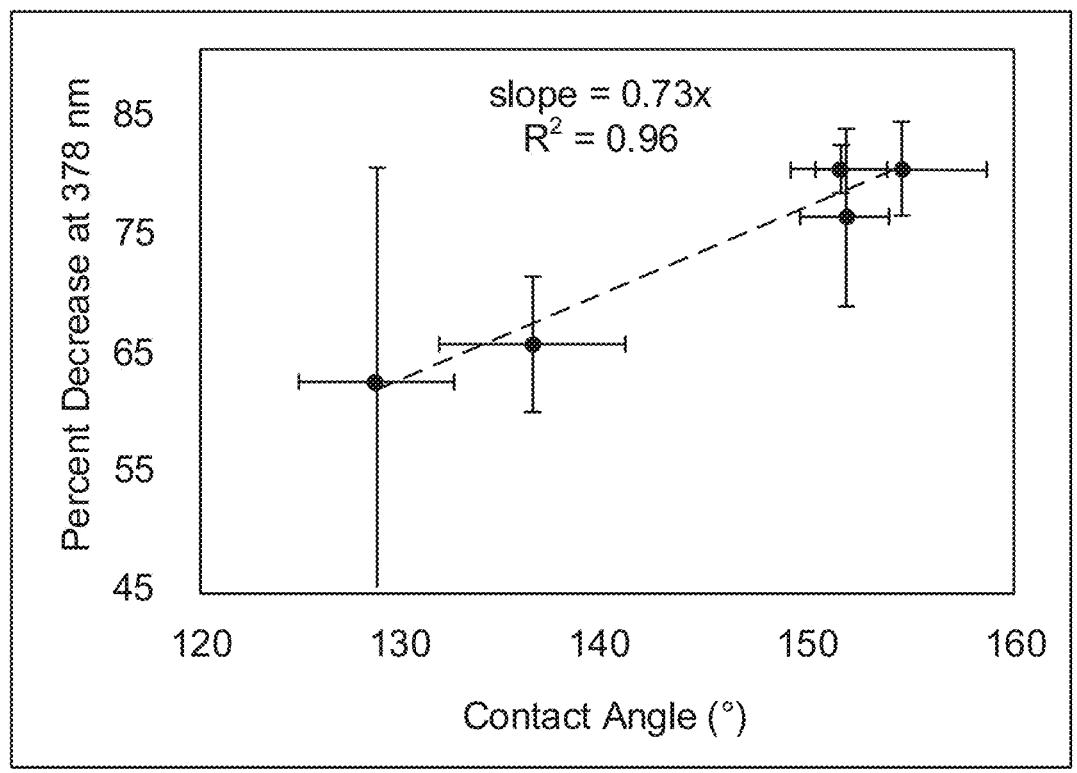
FIG. 17F is a graph showing a relationship between single oxygen production and hydrophobicity.

Referring to FIG. 17F, a relationship exists between the amount of single oxygen trapped and the contact angle of the surface. Five different surfaces (see Table 1) were coated with chlorin e6 sensitizer and the amount of singlet oxygen was measured after 20 minutes of illumination by quantifying the percent decrease of the absorbance of the 9,10-anthracene dipropionate dianion trapping solution in a UV-vis spectrophotometer at a wavelength of 378 nm. As the hydrophobicity of the surface (as measured by increased contact angle) increases, the quantity of single oxygen produced also increases.

Singlet oxygen yield was also changed by sensitizer concentration. Four superhydrophobic surfaces were coated with the photosensitizer chlorin e6. The photosensitizer was applied by brushing a solution of chlorin e6 dissolved in DMSO. The concentration of the photosensitizer in DMSO was varied to control the amount of chlorin e6 deposited on the surface. Solution concentrations varied from 1.5 to 30 mg per mL. The amount of chlorin e6 deposited on the surface was determined by extracting the chlorin e6 from a 2.0 mm diameter surface using either 2.0 or 4.0 mL of DMSO depending on the amount of photosensitizer and then quantified by the absorbance measured by UV-vis spectroscopy. Known concentrations of chlorin e6 in DMSO were used to calibrate the absorbance values. The singlet oxygen yield after 15 minutes of illumination was determined by quantifying the percent decrease of the absorbance of the uric acid trapping solution in a UV-vis spectrophotometer at a wavelength of ~291 nm. The results are shown in Table 2. In one embodiment, the assembly has a surface concentration of at least 60 nmol per square cm. In another embodiment, the surface concentration is at least 200 nmol per square cm. In another embodiment, the surface concentration is at least 300 nmol per square cm. In another embodiment, the surface concentration is at least 600 nmol per square cm. In another embodiment, the surface concentration is at least 900 nmol per square cm.

TABLE 2

| Surface | Ce6 coating solution conc. (mg/mL) | Loading (nmol/surface) | Loading (nmol/cm$^2$) | Singlet Oxygen Yield after 15 minutes (%) |
|---|---|---|---|---|
| Surface A | 3.0 | 7 ± 0.6 | 220 | 26 |
| Surface B | 12.0 | 11 ± 1.0 | 350 | 31 |
| Surface C | 18.0 | 31 ± 2.2 | 990 | 46 |
| Surface D | 30.0 | 35 ± 4.0 | 1100 | 59 |

The described configurations have been found to be effective at killing multi-species biofilms. Three types of bacteria: *S. mutans, A. naeslundi* and *P. gingivalis* cultured on hydroxyapatite discs to form a multi-species biofilm about 80 microns thick. The four superhydrophobic Ce6 coated surfaces (see Table 2) were placed on the biofilm and irradiated for about 15 minutes. The biofilm was removed and the number of CFUs were determined by plating on three different agars. The results are shown in Table 3. Controls included: no PDMS film; chlorhexidine; superhydrophobic PDMS without photosensitizer and without light (SH S−L−); PDMS with photosensitizer and without light; and PDMS with photosensitizer but no light. Results in table below are average values of the three bacteria types comparing the change in CFU numbers between the controls (SH S−L−) and the exposed samples (SH S+ L+).

Similarly, the effective light dose was studied. Superhydrophobic PDMS films coated with chlorin e6 (30 mg/mL coating solution, 1100 nmol/cm$^2$) were used for these experiments performed in the same manner as described above. Irradiation times varied from 4 minutes and 12 seconds for a dose of 100 J/cm$^2$ to 18 minutes and 56 seconds for a dose of 500 J/cm$^2$. The results are shown in Table 4

TABLE 3

| Surface | Ce6 coating solution conc. (mg/mL) | Loading (nmol/cm$^2$) | log CFU reduction - 180 J/cm$^2$ | log CFU reduction - 400 J/cm$^2$ |
|---|---|---|---|---|
| Surface A | 3.0 | 220 | 1.24 | 2.14 |
| Surface B | 12.0 | 350 | 1.85 | 2.75 |
| Surface C | 18.0 | 990 | 2.16 | 3.28 |
| Surface D | 30.0 | 1100 | 2.95 | 4.94 |

TABLE 4

| Light dose (J/cm$^2$) | Loading (nmol/cm$^2$) | log CFU reduction |
|---|---|---|
| 100 | 1100 | 1.34 |
| 180 | | 2.94 |
| 270 | | 3.61 |
| 315 | | 3.37 |
| 400 | | 4.94 |
| 500 | | 4.96 |

These results demonstrate (1) Higher concentration of chlorin e6 on the surface was more effective at killing the bacterial biofilms than lower amounts of chlorin e6 (2) Higher dose of light results in more effective biofilm killing (3) best conditions observed with a superhydrophobic PDMS film prepared with a 30 mg/mL coating solution (1100 nmol/cm$^2$ surface concentration) and a light dose of 400 J/cm$^2$ irradiated through the back side of the PDMS film (4) above 400 J/cm$^2$, it appears that no additional killing is detected, but this may be due to the detection limit of the experiment. A log 5 reduction corresponds to killing 99.999% of all CFUs initially present FIG. 18A (side view) and FIG. 18B (top view) depict an assembly 1800 that is similar to the assembly 1700. The assembly 1800 has an optical fiber 1802 with a first height 1804 that narrows to a second height 1806. The second height 1806 then further narrows to a third height 1808 which is constant over a length 1810 until terminating at a blunt tip 1811. The assembly 1800 has a first width 1812 which narrows to a second width 1814 which narrows to a third width 1816 which is constant over the length 1810.

In one example, the first height 1804 is about 1 mm, the third height 1808 is about 0.5 mm, the first width 1812 is about 1 mm, the third width is about 0.75 mm. A superhydrophobic polymer 1818 is also applied to assembly 1800. The superhydrophobic polymer 1818 follows the height-profile of the optical fiber 1802 (see FIG. 18A) but is rectangular in its width profile (see FIG. 18B). For example, the superhydrophobic polymer 1818 may have a length 1820 of about 7 mm and a width 1822 of about 3 mm. In the embodiment of FIG. 18A, the superhydrophobic polymer 1818 has a pointed tip 1819 proximate the blunt tip 1811. This configuration is advantageous in some applications because the blunt tip 1811 minimizes damage to the superhydrophobic polymer 1818 during use, yet the pointed tip 1819 is easily inserted into a periodontal pocket.

Figure 19A:
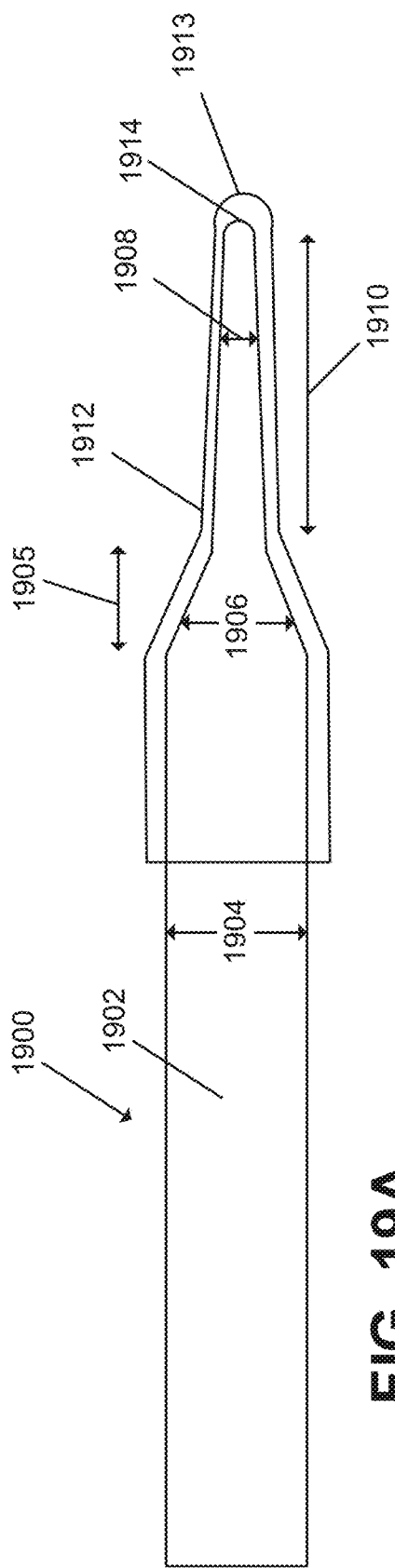
FIG. 19A and FIG. 19B provide a side view and a top view, respectively, of an assembly that uses a blunt-tipped optical fiber in conjunction with a superhydrophobic polymer that provides a blunt tip.
Figure 19B:
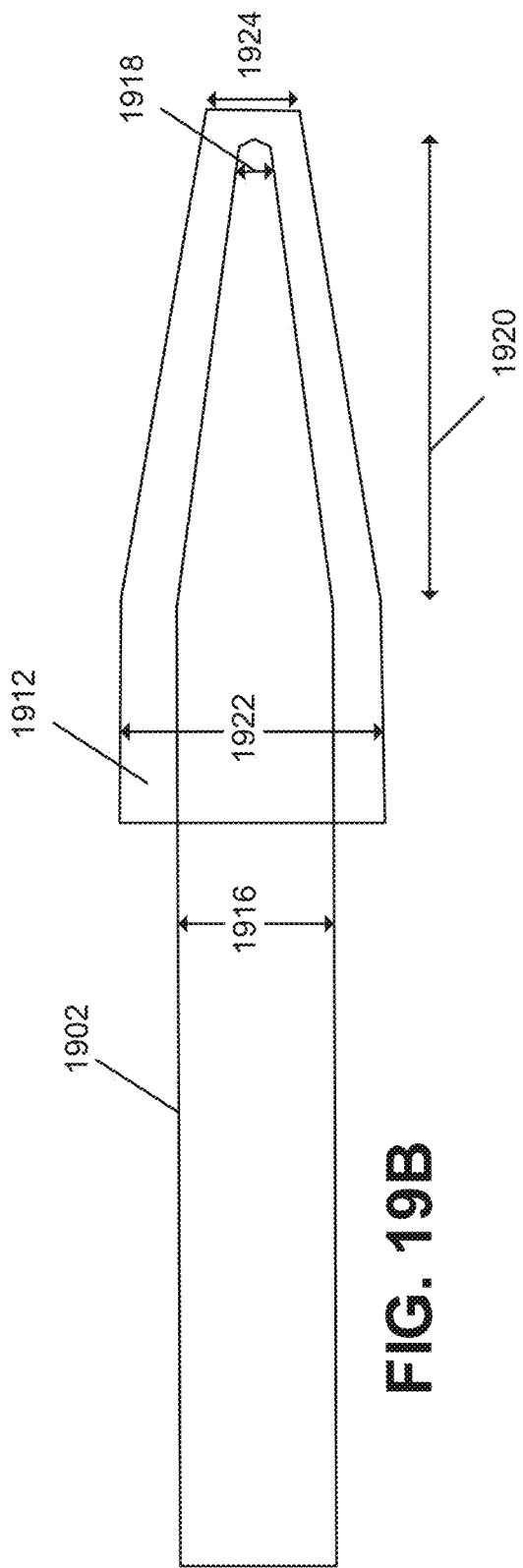

FIG. 19A (side view) and FIG. 19B (top view) depict another embodiment with an assembly 1900. The assembly 1900 has an optical fiber 1902 with a first height 1904 (e.g. 1 mm) that narrows to a second height 1906. The second height 1906 then further narrows to a third height 1908 (e.g. 0.5 mm) which is constant over a length 1910. The transition from the first height 1904 to the third height 1908 occurs over a non-zero distance 1905 (e.g. 1 mm). In the embodiment of FIG. 19A, a superhydrophobic polymer 1912 is present that has a blunt tip 1913 proximate blunt tip 1914 of the optical fiber 1902.

FIG. 19B is a top view of the assembly 1900. The optical fiber 1902 has a first width 1916 (e.g. 1 mm) that narrows to a second width 1918 (e.g. 0.75 mm) over a distance 1920 (e.g. 3 mm). The superhydrophobic polymer 1912 has a width 1922 (e.g. 2.5 mm) that narrows to a second width 1924 (e.g. 1.5 mm) over the non-zero distance 1920.

FIG. 20A (side view) and FIG. 20B (top view) depict another configuration of an assembly 2000 that is similar to the rubber policemen used in laboratories. An optical fiber 2002 is provided that is substantially similar to the other optical fibers described in this disclosure. A superhydrophobic polymer 2004 is provided that is removably attached to the optical fiber 2002. In the embodiment depicted, the superhydrophobic polymer 2004 provides a wedge shape similar to that of superhydrophobic polymer 1712 of FIG. 17A and FIG. 17B. Superhydrophobic polymers with alternate shapes that are described elsewhere in this specification are also contemplated for use in the disclosed embodiment. The superhydrophobic polymer 2004 may be formed from PDMS and provides a tip thickness of about 200 microns. In one embodiment, the PDMS comprises a filler to increase the firmness of the superhydrophobic polymer 2004 and promote light scattering. PDMS that was filler-free was too soft to be inserted in a periodontal pocket and did not scatter light well. Examples of suitable filters include glass particulates and stainless-steel filaments. In one embodiment, the superhydrophobic polymer 2004 is formed from a thermoplastic polymer such as PE, PP, FEP, a cyclic olefine polymer (COP) such as those sold under the trade name ZEONEX®. Such thermoplastics are firmer than PDMS and need not include a filler.

Because teeth are not perfect rectangular solids but have curved surfaces with both concave and convex surfaces the optical probe, in some embodiments, has some mechanical compliance so that it can conform as closely as possible to the tooth surface. One way to obtain compliance is to apply a superhydrophobic elastomer (e.g. PDMS) coating over the relatively rigid PMMA or glass optical fiber. Another approach is to use a relatively compliant optical fiber, such as a MMA co-polymer (TX-POF from Jiangsu TX Plastic Optical Fibers Co.) This soft optical fiber can be treated to be superhydrophobic, or it can be coated with a lower modulus elastomer such as PDMS.

To increase compliance a fiber bundle could be used where each individual fiber is less than 1 mm in diameter. Stiffness is proportional to 1/thickness raised to the $4^{th}$ power. Using an array of individual fine fibers complies more readily to the shapes of the tooth.

The final wedge can be curved so that it could treat multiple surfaces of the tooth at the same time. For example, an "L" shaped wedge could treat the Buccal side of the tooth as well as the region between two adjacent teeth. A "C" shaped wedge could treat the Buccal side and two inter-tooth surfaces at the same time. In theory, an "O" shaped wedge could be made that would treat the entire perimeter of the tooth simultaneously.

In one embodiment, the optical fiber is formed from a hydrophobic polymer, such as FEP. The terminal end of the optical fiber is roughened to produce a superhydrophobic surface which is coated with sensitizer. In this fashion, the superhydrophobic polymer (such as the superhydrophobic polymer 1712) may be omitted. The optical fiber and the terminal end are monolithically formed of the hydrophobic polymer and may be wedge-shaped as described elsewhere in this disclosure.

Medical Bandage

Figure 21A:
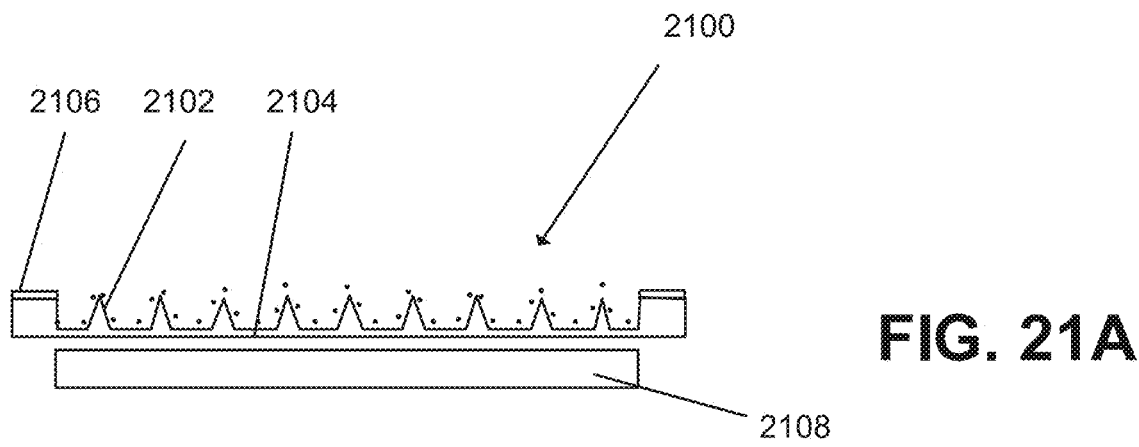
FIG. 21A to 21C depict a bandage that promotes the generation of singlet oxygen.
Figure 21B:
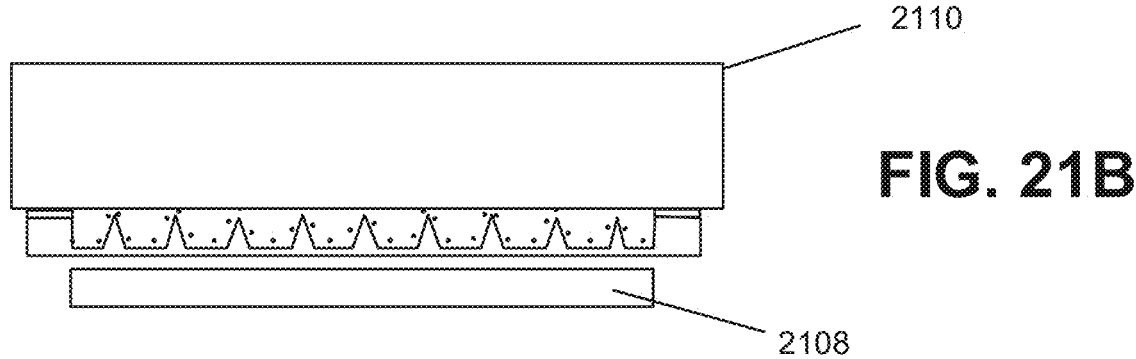
Figure 21C:
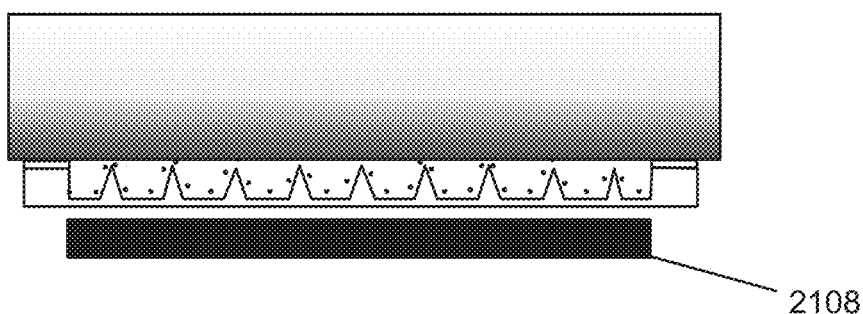

Referring to FIG. 21A-C, a PDT method is also disclosed that uses a bandage 2100. Referring to FIG. 21A, a sensitizer 2102 is loaded onto a superhydrophobic surface that is embodied as a flexible substrate 2104. The flexible substrate can be made of transparent materials for the light generated by LED source, e.g. glass, PMMA, PE, PS, PP, PET, silicone, and other plastic or rubber materials. Hydrophobic modification is required when the substrate is hydrophilic. To achieve superhydrophobicity, the flexible substrate 2104 is coated with a hydrophobic polymer such as polydimethylsiloxane (PDMS), fluorinated ethylene propylene (FEP), polyethylene (PE) or similar polymer. The polymer surface is formed such that an array of micro and/or nano-scale protrusions renders the surface superhydrophobic. Such superhydrophobic surfaces are known in the art. Also see the flexible substrates discussed elsewhere in this disclosure. The micro/nano structures on the superhydrophobic surface can effectively scatter light, and thus can improve the uniformity of the light intensity in the treated area. The sensitizer can be loaded onto a superhydrophobic surface by physical deposition methods such as dip-coating, spraying, or brushing of sensitizer solutions. A solvent such as DMSO may be appropriate as the solvent can partially wet the superhydrophobic surface and traces of residual solvent would not be harmful to the patient. The sensitizer can also be covalently bonded to superhydrophobic surfaces. Alternatively, the sensitizer can be absorbed onto or covalently bonded to micro/nano particles at first, and then the micro/nano particles loaded with sensitizer can be anchored onto superhydrophobic surfaces.

A bio-adhesive 2106 can be used to adhere the bandage 2100 to a patient's skin 2100 (FIG. 21B). The bio-adhesive 2106 provides a frame (e.g. the bio-adhesive 2106 circumscribes the sensitizer 2102) that attaches the bandage onto the skin like conventional bandages. The superhydrophobic surface with frame encapsulation plays three important roles. First, a large amount of air including oxygen is trapped in the pores of the superhydrophobic surface, providing the necessary oxygen source. Second, it enables uniform delivery of the generated reactive oxygen species to the tissue as well as prevents the loss of the photo-generated singlet oxygen caused by environmental air flow or patient body movement. Third, it acts as a spacer to reduce the contact force as well as the contact area between the micro/nano protrusions and the skin tissue.

As shown in FIG. 21B, only the sensitizer on the tips of micro/nano protrusions is in direct contact with the skin 2110. These points of contact occupy a small portion of the total surface area of the bandage, e.g. <10% of the whole surface area. This can prevent the unconformable feeling and greatly improve the patient treatment experience. If desired, the tips of the protrusions can be coated with PDMS, or another passive polymer, so that no sensitizer directly contacts the skin. Moreover, a thin permeable membrane, such as a porous polyethylene membrane with 0.2 microns pores, can be applied to the bandage over the superhydrophobic surface to prevent all direct contact between sensitizer and skin.

In FIG. 21C, light is transmitted from a light source 2108, through the backside of the flexible substrate 2104 so that it can illuminate the sensitizer 2102 and generate airborne singlet oxygen. The singlet oxygen then can diffuse across and interact with the skin 2110 of a nearby patient. This is quite different from traditional PDT treatment where the sensitizer is injected or applied directly onto the skin where it can be absorbed. The light source can be white light or arrays of LED light at specific wavelengths correlating to the sensitizer. The light source can also be thin, electroluminescent light source, e.g. VYNEL™ HD light strips. The light source can be external to the bandage or can be fully integrated into the bandage. Flexible electroluminescent light sources can be especially practical for long-term applications.

The disclosed method has another advantage in that the light is preferentially absorbed by the sensitizer and so it reduces undesired light/heat absorption by skin tissue, which could cause burns, pain or itching during PDT treatment. Additionally, traditionally PDT methods leave residual sensitizer on the skin or inside the body and these can continue to produce singlet oxygen after the treatment is over which is often undesirable. Therefore, the disclosed method can greatly improve the completeness of PDT treatments. Advantageously, most of the light is absorbed by the sensitizer and only a small portion of light can reach the skin. This can significantly reduce the onset of side-effects such as burns, pain or itching, and can greatly improve the completeness of PDT treatments.

The singlet oxygen produced by the sensitizer coated on the lower portion of the bandage surface are in vitro singlet oxygen, and can diffuse to the infected areas through openings (i.e. plastron) provided by the micro/nano structures on the superhydrophobic surfaces. The dose of singlet oxygen can be adjusted by changing the amount of sensitizer coated onto the superhydrophobic surface, the light intensity as well as the light illumination time. The PDT can be stopped at any moment by simply turning off the light illumination and/or removing the bandage from the tissue. Thus, the bandage 2100 enables a quick response to early onset adverse events. This is because the sensitizer is attached to the bandage 2100 and is not administered into the patient or applied onto the patient's tissue. In one embodiment, a light blocking layer is placed on the outside surface of the bandage to prevent accidental generation of singlet oxygen from room light or sunlight. A reflective layer may be placed external to the integrated light source (e.g. electroluminescent panel). This layer reflects additional light onto the sensitizer generating additional singlet oxygen as well as blocks external room light or sunlight from generating singlet oxygen when it is not desired.

Figure 22A:
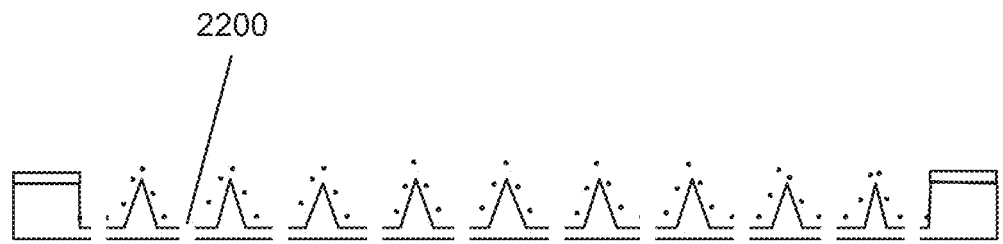
FIG. 22A to 22C depict a bandage with through-holes at various positions on the bandage.
Figure 22B:
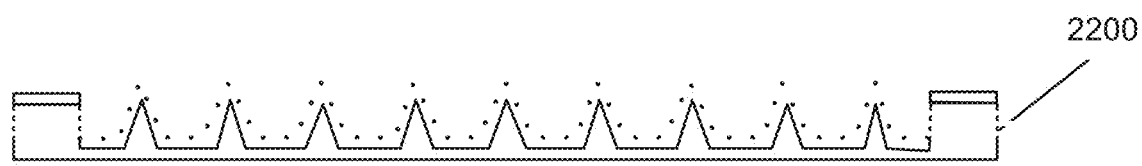
Figure 22C:
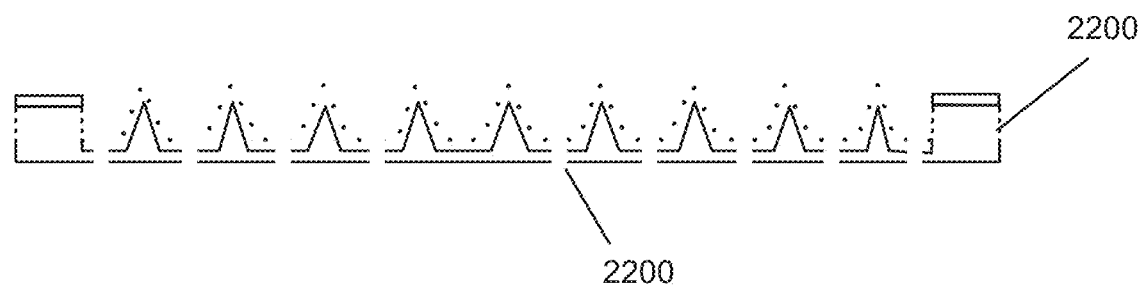

Referring to FIGS. 22A-C, through-holes 2200 can be created in a bandage 1800 to enhance the ingress of ambient oxygen. This also adjusts the humidity in the covered area. Through holes 2200 can be created on the bottom of the superhydrophobic surface (FIG. 22A), at the sides of the superhydrophobic surface (FIG. 22B) or both (FIG. 22C). The size of the holes can range from 1 to 500 µm.

Figure 23:
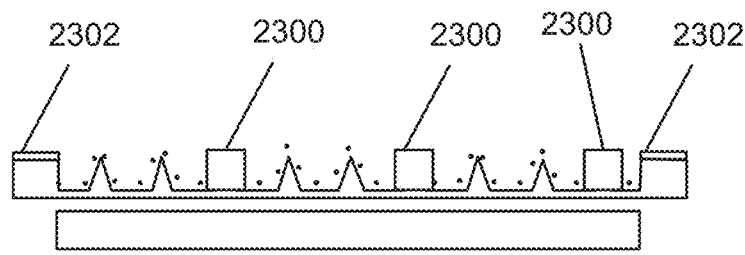
FIG. 23 depicts a bandage with ridges disposed within the bandage perimeter.

Referring to FIG. 23, ridges 2300 can be added within the perimeter of the frame of the superhydrophobic surfaces for large area skin treatment. The distance between ridges can ranges from 1 cm to 5 cm and the frame is defined by the bio-adhesive 2302. The ridges 2300 keep the superhydrophobic surface from becoming compressed against the skin. When the span across the bandage becomes too large, the bandage sags (or becomes susceptible to being squeezed) and a larger surface area fraction of the superhydrophobic surface contacts the wound. Because the PDMS is compliant, areas of the surface may become sealed off from air—and so the amount of singlet oxygen generated would be lower than expected. To minimize the contact area between bandage and wound to facilitate healing and bandage removal ridges may be added that resist compression to ensure that the superhydrophobic surface just touches the wound at its highest points and so minimizes the physical contact between bandage and wound. In some embodiments, this also permits one to know the dose of singlet oxygen delivered.

Figure 24A:
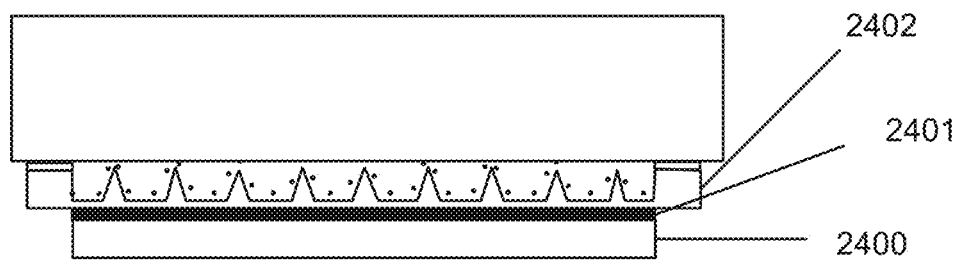
FIG. 24A and FIG. 24B a bandage with two examples of light source placement.
Figure 24B:
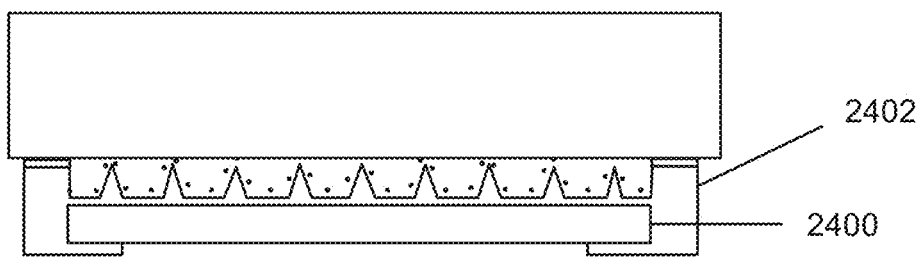
Figure 25:
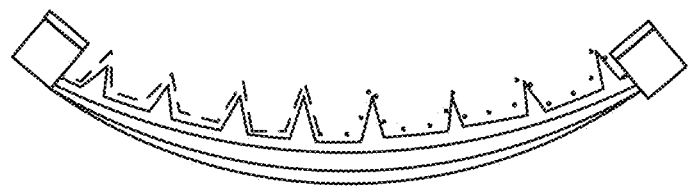
FIG. 25 depicts a bandage that is curved to better conform to a curved surface of a patient's body.

The light sources, power supply/batteries and control panels can be integrated for convenient portable treatment. In this case, consumables including the superhydrophobic carrier with sensitizer and the batteries can be designed to be replaceable. Adhesives or mechanical hooks can be used to align and hold the components. Two examples are shown in FIG. 24A and FIG. 24B, respectively. In FIG. 24A, the light source 2400 is held to the flexible substrate 2402 with an adhesive 2401. In FIG. 24B, the light source 2400 is held to the flexible substrate 2402 by mechanical hooking. This portable device can be flexible and compliant to the contours of the body. This portable device has advantages in periodic dosing control treatment. The light source can be programmed to turn on for a specific length of time (e.g. 2 minutes) followed by a specific dark time (e.g. 10 minutes). Several PDT studies have shown that periodic illumination during PDT treatment is more effective than continuous illumination. The light sources, power supply and control panels can also be separated from each individual PDT device so that patient can share the light sources, which could reduce the costs per treatment. Referring to FIG. 25, the bandage can be designed with a curved shape to be compliant to the contours of the body.

Singlet Oxygen Generator for Recirculating Aquaculture System Applications

In another embodiment, a Singlet Oxygen Generating (SOG) system is provided that safely kills pathogens while simultaneously ensuring full oxygen saturation levels in either new or recirculated water. Such a SOG system may be useful in large-scale applications (such as municipal drinking water) or small-scale applications (such as home drinking water or personal drinking water). The disclosed SOG system would be especially useful for Recirculating Aquaculture Systems (RAS) used to raise fish commercially because it is effective in killing microorganisms in turbid water. This SOG combines visible light, a chemical stable sensitizer and ground state molecular oxygen to generate singlet oxygen. Singlet oxygen has been shown to effectively inactivate virus, bacteria, fungi, as well as cancerous cells. Only visible light is used that is economically supplied by electrically efficient LED devices that operate at low voltage of less than 4 volts dc). Moreover, singlet oxygen systems are safe for fish and humans. The singlet oxygen excited state is sort-lived, rapidly decaying back to the ground state (half-life: <100 ms in the gas phase; <4 μs in water). The ground state of molecular oxygen is safe to breath. Because pathogens accumulate at the air-water interface of a bubble, bubbles containing singlet oxygen effectively kills pathogens within their short lifetime. In the disclosed SOG, the sensitizer is isolated from contacting the water using a superhydrophobic support system. Thus there is no potential for sensitizer molecules to dissolving into the water.

Figure 26:
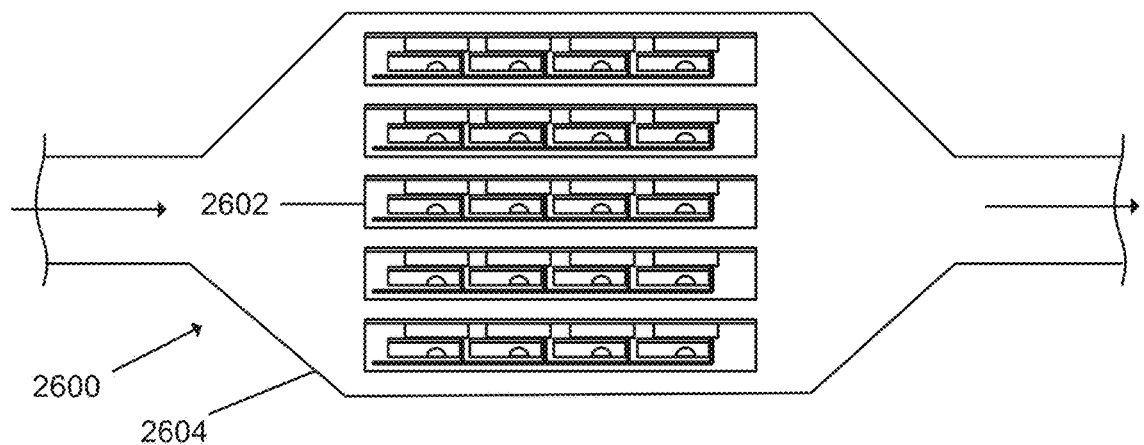
FIG. 26 and FIG. 27 depict a singlet oxygen generator system for use in a Recirculating Aquaculture System.

FIG. 26 illustrates a SOG showing a plenum containing an array of ten fins immersed parallel to the water flow direction. The SOG system is comprised of an array of fins immersed in water that generate singlet oxygen bubble plumes. Air, or pure oxygen, is supplied to each fin that is internally illuminated with LEDs. Oxygen contacting the sensitizer supported within the fin is excited to the singlet state which then exits into the flowing water stream as a plume of singlet-oxygen containing bubbles. The number and size of the fins can be easily scaled to accommodate the flow rate of the RAS system. A 1 cubic meter SOG system is estimated to treat 500,000 gallons of water per day, inactivating pathogens as well as saturating the water with oxygen. These devices will increase the health of fish raised in intensive RAS systems, lower capital and operational costs, and so increase profits for farmers.

Figure 27:
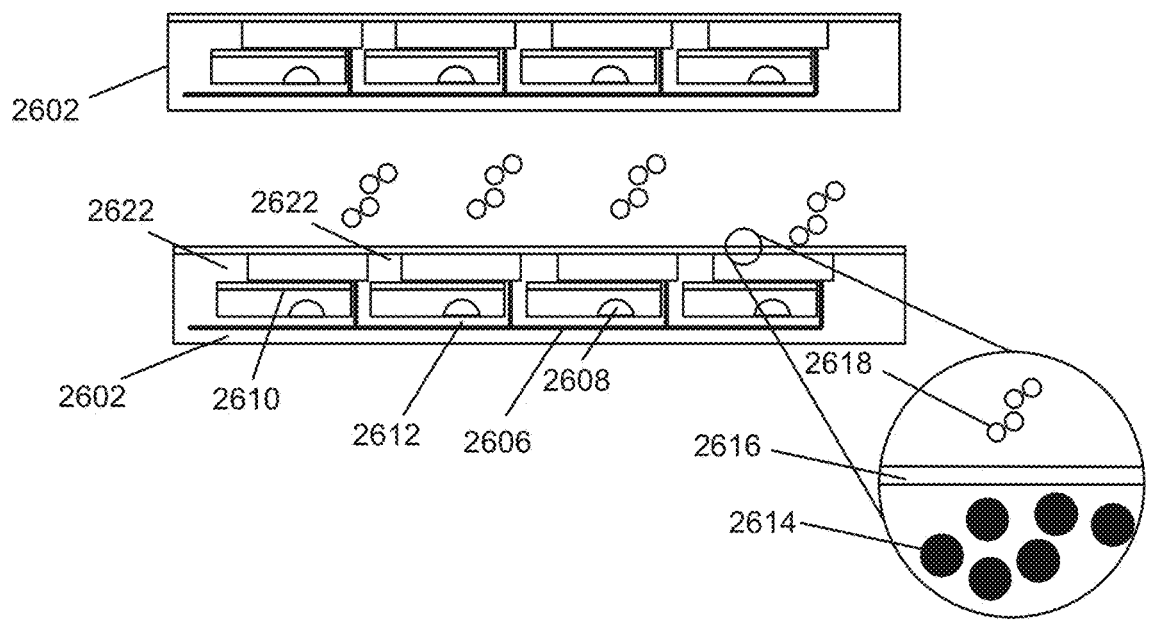

FIG. 26 and FIG. 27 show a cross section schematic of a SOG system 2600. The system 2600 comprises an array of longitudinal fins 2602 in a square plenum 2604. Continuous streams of singlet oxygen ($^1O_2$)-containing bubbles are ejected through gas supply tubes 2606 into the flow of water along the periphery of each fin. High-intensity light emitting diodes (LEDs) 2608 are positioned along the fins 2602 and route light of the appropriate wavelength through a light-scattering layer 2610 in the middle of the fins as shown. The light scattering layer may be, for example, PDMS in which silica nanoparticles are dispersed to scatter the light. Alternatively, the scattering layer could be a superhydrophobic layer of FEP or PDMS with surface features formed by roughening which may be stochastic or symmetrically applied to the surface and may be of any shape that results in light scattering including conical pyramids, cylinders, rectangles, parallel ridges, etc. The surface features may be of uniform size and shape, or more may have a hierarchical structure. The surface features enable the scattering of light to improve the uniformity of excitation of the sensitizer particles 2614. The superhydrophobic light-scattering layer may also serve as the support for the sensitizer particles 2614. The LEDs are mounted to a thermally conductive substrate 2612 so that the heat generated by the LEDs may be easily dissipated into the flowing water. In one embodiment, the thermally conductive substrate 2612 is an aluminum substrate. In another embodiment, the thermally conductive substrate 2612 is a corrosion-resistance materials such as brass of stainless steel. Stand-offs 2622 separate a (porous) layer of sensitizer particles 2614, illuminated by the light, from an outer membrane 2616 made of a porous, hydrophobic polymer. The porous, hydrophobic polymer can be, for example, polyethylene, ultra-high molecular weight polyethylene (UHMWPE), FEP, PTFE, PVDF, or any polymer on which water makes a contact angle of 90 degrees or greater. Pressurized air or oxygen flows over the illuminated sensitizer particles on the surfaces of which singlet oxygen is generated. The singlet oxygen molecules exit from the fins as a continuous stream of bubbles 2618. The rate at which bubbles leave the membrane and their characteristic size are controlled by the air pressure and pore distribution in the polymer membrane. Since the outer surface of the polymer is hydrophobic, the singlet oxygen generator is not exposed to water. The support surface for the sensitizer may be superhydrophobic, which would provide an additional barrier to prevent water from contacting the sensitizer directly.

Once ejected from the generator, the bubbles ascend and interact with particles (e.g. virus, bacteria, algal microorganisms) suspended in water. It is well known that these microorganisms preferentially accumulate at the air-water interfaces of bubbles because of the wetting properties of these particles. Depending on the water contamination level, there are two limiting cases regarding the mobilization of bubble-water interface. For pure water, the interface is fully mobilized (slip condition applicable) and singlet oxygen diffuses from the bubbles into the water creating an effective annulus around the bubbles. For highly contaminated water, microorganisms accumulate on the bubble surface, forming a fully immobilized interface similar to that of a solid sphere. Thus the microorganisms will directly contact, and will be killed by, the singlet oxygen contained within the bubble. In reality, the mobilization is somewhere in between these two cases.

In Situ Generation of Singlet Oxygen in Chemical Synthesis

Photogenerated singlet oxygen is not only useful in photodynamic therapy, it is commonly used in the synthesis of oxygenated chemicals. Even though singlet oxygen is a short-lived excited state of molecular oxygen, it is a practical reagent for compound oxidation and can form carbon-oxygen and heteroatom-oxygen bonds. For example, singlet oxygen reactions for generating oxygenated compounds, including endoperoxides from [2+4] cycloadditions, dioxetanes from [2+2] cycloadditions, hydroperoxides from 'ene' reactions of alkenes, hydrazones, DNA bases and amino acids, including methionine sulfoxide from methionine.

Traditional singlet oxygen is formed by dissolving the sensitizer and oxidizable compound into solution and irradiating the sensitizer with a light in the presence of oxygen to oxidize the compound. This traditional singlet oxygen synthetic method requires the separation of the sensitizer after reaction, can leave behind photobleached sensitizer fragments, and/or produce unwanted side-reactions with oxygen radicals. Appending the sensitizer to a solid superhydrophobic surface of a magnetic stir bar, paddle or other support using an internal light source helps to facilitate synthetic compound oxygenation, by absence of sensitizer in solution without required removal and unwanted oxygen-radical side reactions. The sensitizer residing on the magnetic stir bar and paddle will continuously produce singlet oxygen with its internal light supply, leading to an improved method for harnessing it for synthetic applications in both small-scale and large-scale reactions.

Figure 28A:
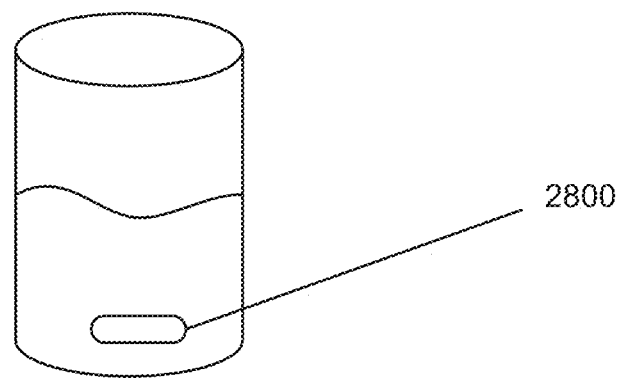
FIG. 28A and FIG. 28B depict a magnetic stir bar that generates singlet oxygen.
Figure 28B:
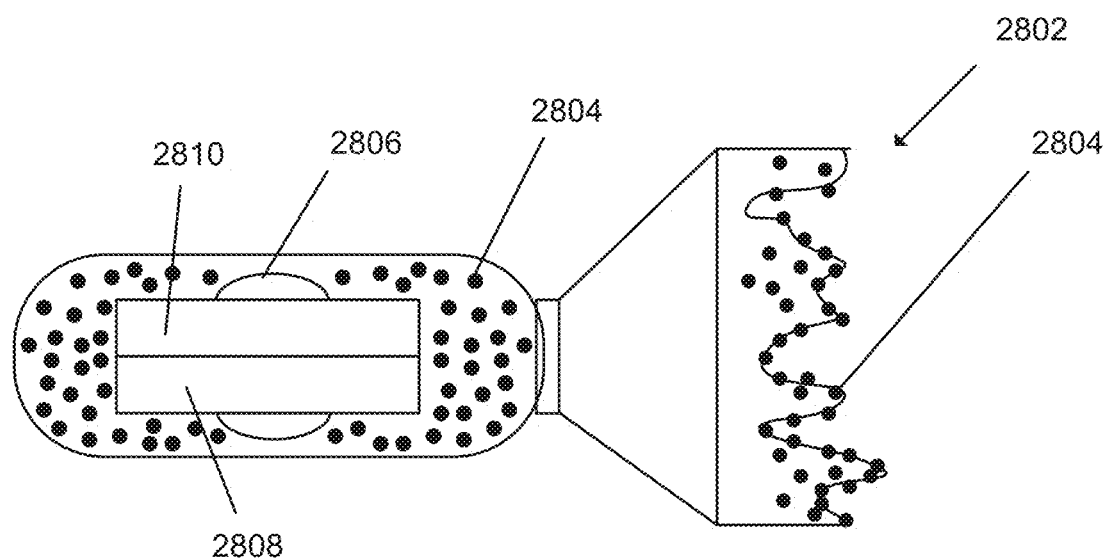

Referring to FIG. 28A and FIG. 28B, a magnetic stir bar 2800 for laboratory-scale synthetic reactions is shown. The components of the stir bar include a magnet 2810, a superhydrophobic exterior surface 2802 bound to a sensitizer 2804, and an internal light source 2806 of an appropriate wavelength that overlaps with the sensitizer light absorption spectra. In one embodiment, the light source is an LED powered by a small battery 2808 (e.g. a size 10 hearing aid battery that measures 5.8×3.6 mm or a battery that is used to power wireless ear buds such as those used in Apple AirPods). The battery may be rechargeable (e.g. based on NiMH or Li-ion chemistry) and be connected to a coil within the-stir bar so that it could be recharged wirelessly by an external coil. The light source may be turned on and off using a magnetically actuated switch. In one embodiment, the relay element of the switch is made of a magnetic material (e.g. iron) and an external magnet displaces the relay element to activate the switch. Alternatively, the LED may illuminate whenever the battery was sufficiently charged. A magnetic is used, which will drive the stir bar by rotation. The photostability of sensitizers increase when residing on heterogeneous surfaces compared to when they are dissolved in a solution as a soluble sensitizer. The stir bar is easily inserted into solution and easily removed after use with no need for chromatography to separate the sensitizer and by-products, that otherwise contaminate the solution.

The stir bar delivers light from an internal LED in the core of the stir bar, in which a magnet will be also located within the core of the bar. The stir bar shape can be ellipsoid to facilitate rotation in a round bottom flask. A magnetic plate is used with the magnetic stirrers, which will drive the stir bar by rotation. In another embodiment, the light source is omitted from the stir bar and is external to the flask. If the flask is opaque, a window in the flask allows illumination of the stir bar from a LED or other external light source. In some embodiments an optical fiber bundle transmits the light from a remote light source to the reaction flask.

Figure 29:
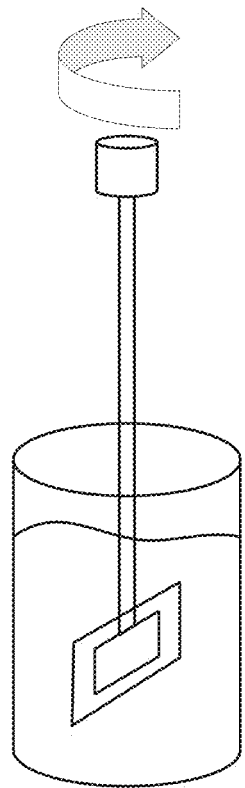
FIG. 29 and FIG. 30 depict stir paddles that generate singlet oxygen.

Referring to FIG. 29, the device can also be configured into a mechanical paddle for pilot-scale or larger synthetic reactors. The paddle is attached to a rod carrying light delivered by an optical fiber. Alternatively, LED light sources can be incorporated into the paddle and illuminated using either internal batteries or an external electrical cable. A gas supply tube that traverses down the rod connecting compressed air or oxygen to the paddle may be used if supplemental oxygen is required. The paddle surface is made to be superhydrophobic and coated with a sensitizer that generates singlet oxygen upon illumination using the appropriate wavelength of light. The source of ground-state molecular oxygen is the air entrapped in the superhydrophobic coating (i.e. plastron). Supplemental oxygen can be provided by a gas supply tube connected to the paddle or by bubbling oxygen into the solution resulting in dissolved oxygen in the reactor liquid. The superhydrophobic mixing blades could be permanently affixed to the mechanical stirring rod, or these blades could be removable so that different sensitizers could be used, depending upon the solvent or wavelength of the light source.

When the internal light is on, photons are delivered from the light emanating from the core of the stir bar or paddle to the superhydrophobic outer surface where it is absorbed by the sensitizer coating. Singlet oxygen, generated at the surface by the sensitizer, is delivered into the surrounding solution where it reacts with substrate compounds. By attaching the singlet oxygen generating surfaces (e.g. paddles) to a mixing device, reactant molecules will be able to collide with singlet oxygen molecules before the reactive singlet oxygen decays back to the ground state. Since the lifetime of singlet oxygen is of the order of 4 microseconds in aqueous solutions, mixing is highly desirable for this device to work with high efficiency. If a sensitizer-coated superhydrophobic substrate was inserted into a reaction kettle such that the surface did not move, only a small percentage of the reactants would react with singlet oxygen. This is because the reactant molecules would be depleted near the static singlet-oxygen generating surface; further reaction would be limited by the diffusion rate of reactant molecules from the bulk of the solution. Even if the reactant solution was mixed by a separate stirring mechanism, the reaction rate would still be limited because of the static fluid boundary layer that would develop adjacent to the singlet-oxygen generating surface. One other embodiment is a jet-impingement mixing system where the static boundary layer would become sufficiently thin that the reaction would no longer be diffusion limited.

In both the stir bar and paddle embodiments, the sensitizer absorbs the light emitted by the light source. Most of the compounds of interest in synthesis do not absorb light in the long wavelengths of the sensitizer. This is an important factor since the light source will excite the sensitizer to generate singlet oxygen, but not be of sufficient high energy to excite substrate compounds for the selective formation of singlet oxygen in the device to improve synthetic access to compound oxygenation.

In both the stir bar and paddle embodiments singlet oxygen generating surface is fabricated using an optically transparent and preferably hydrophobic material. Polydimethylsiloxane (PDMS) is a good substrate material because it is transparent, hydrophobic and chemically inert to most compounds. Other transparent and hydrophobic polymers would also be suitable substrates, such as polyethylene and polypropylene. Polymers that exhibit transparency, hydrophobicity, chemical stability and high temperature stability would be especially preferred, such as: fluorinated ethylene propylene (FEP), polytetrafluoroethylene (Teflon or PTFE) and composites fabricated with these fluoropolymers.

The exterior of the mixing paddle or stir bar is made to be superhydrophobic by forming a rough surface on these materials. Roughening techniques include additive techniques (e.g. 3D printing), subtractive techniques (e.g. sandblasting, machining) as well as the formation of features during fabrication (e.g. casting, molding). Features formed by roughening may be stochastic or symmetrically applied to the surface and may be of any shape including conical pyramids, cylinders, rectangles, parallel ridges, etc. The features may be of uniform size and shape, or more preferably have a hierarchical structure. The micro-textured surface enable the scattering of light to improve the uniformity of excitation of the sensitizers on the outer surface. The light source may be, for example, an LED. The paddle surface will be driven by an externally coupled motor.

The sensitizer can be loaded onto the superhydrophobic surface by adsorption, including deposition with solvent evaporation or brushing of the sensitizer dissolved in DMSO solution onto the superhydrophobic surfaces. The sensitizer can also be covalently bonded to superhydrophobic surfaces with the use of silane chemistry, and its loading quantity determined by silica dissolution with established hydrofluoric acid techniques.

Figure 30:
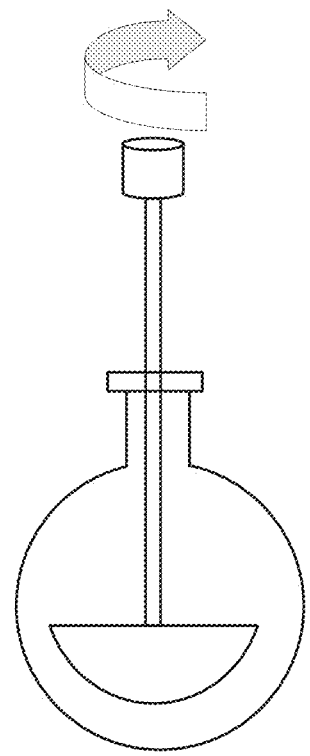

The light source can be white light LED or an LED with wavelength output range that overlaps the sensitizer absorption for facile excitation of the sensitizer, and thus efficient formation of singlet oxygen. The light source can also be a white light source with the photons directed into an optical fiber for the paddle system. The paddle device can be designed with a curved paddle shape to conform to round bottom flasks as shown in FIG. 30.

Maintenance of Heat Exchangers

Another application is for the cleaning and maintenance of heat exchangers. Biofouling poses a significant challenge to marine systems. Microorganisms present in water accumulate on wetted surfaces contaminating and blocking the flow and causing mechanical failures. Conventional antifouling methods often include chemical treatment and physical scrubbing which cause undesirable environmental consequences and require high maintenance cost. Biofouling can be reduced or eliminated using a singlet oxygen bubble generator. Many ships, for example, have heat exchangers where heat from the engine and other components aboard a ship are dissipated into the water using a tube heat exchanger. Seawater is pumped through the tubes to extract heat from ship-board fluids (e.g. motor oil). Devices such as the disclosed magnetic spin bar can be introduced such that they travel through the tubes and kill microorganisms before they can develop into thick biofilms that reduce the flow of water and/or reduce the heat transfer from the oil to the seawater. The magnet can be used to extract the singlet oxygen generating (SOG) spheres or ellipsoids before they are ejected into the ocean. In this way they can be recovered, recharged and reused. If the heat exchanger system is magnetic, then the magnets can be excluded from the SOG devices. A filter system would then be used to recover the SOG devices from the salt water.

Self-Sterilizing Surfaces

Figure 31:
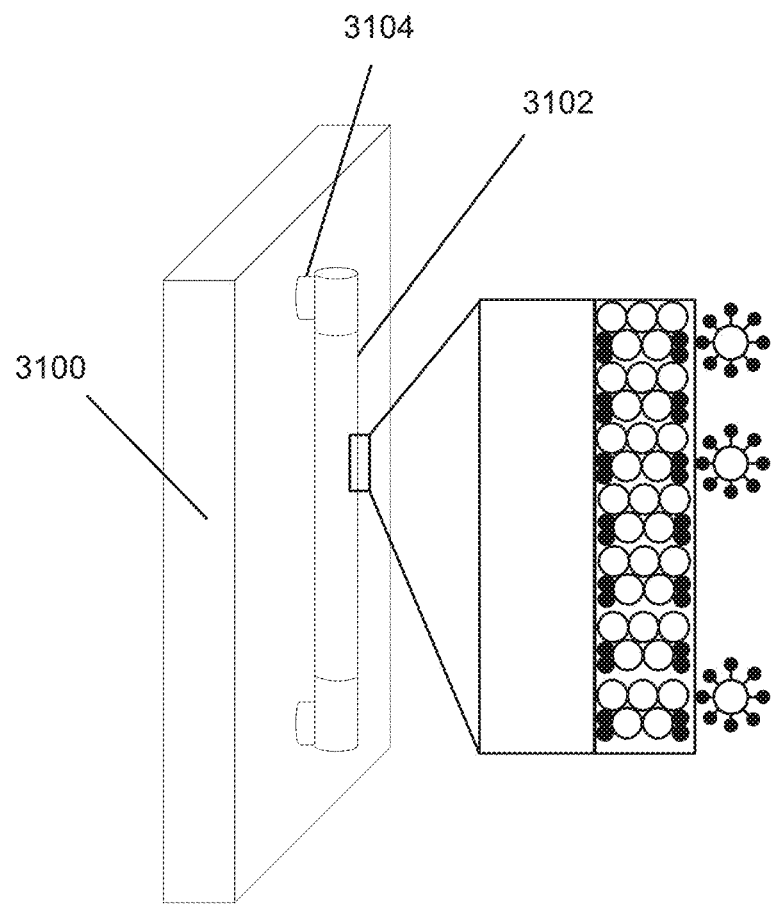
FIG. 31 is a door pull that uses singlet oxygen to self-sterilize.

In one embodiment, singlet oxygen generation is used to produce a self-sterilizing surface. For example, FIG. 31 depicts a door 3100 that connects to a door pull 3102 by two supports 3104. The two supports 3104 are disposed at a proximal end, and a distal end, of the door pull 3102. The door pull 3102 may be formed of a rigid, transparent substrate such as glass (soda-lime glass, low-iron soda-lime glass, borosilicate glass, etc), PMMA, polystyrene, polystyrene copolymers (e.g. with acrylonitrile) or high-impact polystyrene, polycarbonate, polypropylene, PDMS (silicone rubber), Cyclo Olefin Polymer (COP), fluorinated ethylene propylene (FEP), PTFE, or the like.

The surface of the door pull 3102 has a high degree of roughness. Techniques such as grit-blasting, sandpaper, chemical etching, laser ablation, machining, sintering, printing and plasma spray can be used to roughen the surface. This creates recesses that can be coated with sensitizer. The roughness also helps scatter light. In some cases, the external surface of the door pull 3102 is made from sintered glass particles such as VYCOR® 7930 glass made of 96% $SiO_2$ and 3% $B_2O_3$ with an internal surface area of 250 $m^2/g$ and void space of 28% by volume, or Varapor porous glass made of >99% $SiO_2$ with a surface area of 100 $m^2/g$ and a porosity of 40% and 10 nm average pore size, or 7176 sintered glass discs supplied by Ace Glass with average pore size of 4-8 microns. In some cases the surface will be made by sintering hydrophobic polymer particles together to make a solid porous rod or a hollow porous tube. Alternatively, the polymer particles can be sintered onto the surface of a solid tube of the same polymer. The pore size after sintering would be less than 10 microns, or more preferentially less than 1 micron or more preferentially less than 0.1 microns.

Sensitizers can be applied to the surface using known methods, including dissolving or suspending the sensitizer in a solvent, coating the mixture and then permitting the solvent to evaporate. In some embodiments the surface is chemically treated so that a covalent bond is formed between the surface and the sensitizer.

A light source, such as a LED may be mounted proximal to the sensitizer. In the case of the door pull 3102 or vertical subway poles, the transparent substrate may be in the form of a hollow tube and the LED is disposed within the hollow tube. The LEDs can be mounted at the ends of the tube so that the interior of the tube acts like a light guide. In some applications the interior of the tube is filled with a light-scattering material that will uniformly illuminate the length of the touched surface. The presence of the light will alert users that active sterilization is in effect. The absence of light will alert users that the surfaces are not being sanitized. The color of the light can be modified to alert owners/operators of the need to change batteries, or other maintenance needs. In some embodiments, air or oxygen is pumped into a plenum below a flat surface, or into the center of a hollow tubular surface. This air or pure oxygen will ensure sufficient oxygen is available to generate singlet oxygen.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An assembly for treating a periodontal pocket, the assembly comprising:
   an elongated optical fiber with a first width and a first height at a distal end and a second width and a second height at a proximal end, wherein the first height is greater than the second height;
   a superhydrophobic polymer coating a terminal portion of the elongated optical fiber at the proximal end, wherein the superhydrophobic polymer is optically transparent and has a roughened surface with a water contact angle of at least 140°;
   a sensitizer disposed on at least a surface of the superhydrophobic polymer, wherein the sensitizer converts triplet oxygen to singlet oxygen upon exposure to light.

2. The assembly as recited in claim 1, wherein the second width is greater than the first width.

3. The assembly as recited in claim 1, wherein the superhydrophobic polymer has a thickness between 50 and 500 microns.

4. The assembly as recited in claim 1, wherein the first width is greater than the second width, thereby forming a narrowed terminus at the proximal end.

5. The assembly as recited in claim 4, wherein the superhydrophobic polymer has length with a constant width over the length.

6. The assembly as recited in claim 4, wherein the superhydrophobic polymer has a length with a width that changes over the length.

7. The assembly as recited in claim 4, wherein the first width of the optical fiber is 1 mm.

8. The assembly as recited in claim 1, wherein the superhydrophobic polymer is selected from a group consisting of a polydimethylsiloxane (PDMS), a fluorinated ethylene propylene (FEP) and a polytetrafluorethylene (PTFE).

9. The assembly as recited in claim 1, wherein the roughened surface has first indentations with a first diameter of 1-20 microns and second indentations with a second diameter of 40-300 microns.

10. The assembly as recited in claim 1, wherein the water contact angle of the roughened surface is at least 150°.

11. The assembly as recited in claim 1, further comprising a light source operatively connected to the elongated optical fiber for delivering light through the elongated optical fiber, through the superhydrophobic polymer and to the sensitizer.

12. The assembly as recited in claim 1, wherein the sensitizer is present at a surface concentration of at least 60 nanomoles per square centimeter.

13. The assembly as recited in claim 1, wherein the sensitizer is present at a surface concentration of at least 600 nanomoles per square centimeter.

14. An assembly for treating a periodontal pocket, the assembly comprising:
    an elongated optical fiber with a first width and a first height at a distal end and a second width and a second height at a proximal end, wherein the first height is greater than the second height;
    a superhydrophobic terminal portion of the elongated optical fiber at the proximal end, wherein the superhydrophobic terminal portion is optically transparent and has a roughened surface with a water contact angle of at least 140°;
    a sensitizer disposed on at least a surface of the superhydrophobic terminal portion, wherein the sensitizer converts triplet oxygen to singlet oxygen upon exposure to light.

15. The assembly as recited in claim 14, wherein the elongated optical fiber and the superhydrophobic terminal portion consist of a monolithic hydrophobic polymer.

16. A method of treating a periodontal pocket, the method comprising steps of:
    inserting, into a periodontal pocket, the proximal end of the assembly of claim 1;
    illuminating the elongated optical fiber with a light source such that light contacts the sensitizer;
    permitting the sensitizer to change ambient oxygen to singlet oxygen within the periodontal pocket.

* * * * *

UNITED STATES PATENT AND TRADEMARK OFFICE
CERTIFICATE OF CORRECTION

PATENT NO. : 11,918,823 B2
APPLICATION NO. : 17/099273
DATED : March 5, 2024
INVENTOR(S) : Alan M. Lyons, Alexander Greer and QianFeng Xu It is certified that error appears in the above-identified patent and that said Letters Patent is hereby corrected as shown below:

In the Specification

Column 1, Line 13, should read:
STATEMENT OF FEDERALLY SPONSORED RESEARCH OR DEVELOPMENT
This invention was made with Government support under grant numbers 2R44DE026083-03 and 1R41DE026083-01A1 awarded by the National Institute of Health. The government has certain rights in the invention.

Signed and Sealed this
First Day of October, 2024

Katherine Kelly Vidal
*Director of the United States Patent and Trademark Office*